(12) United States Patent
Brimble et al.

(10) Patent No.: US 7,776,876 B2
(45) Date of Patent: *Aug. 17, 2010

(54) CYCLIC G-2ALLYLPROLINE IN TREATMENT OF PARKINSON'S DISEASE

(75) Inventors: Margaret Anne Brimble, Auckland (NZ); Jian Guan, Auckland (NZ)

(73) Assignee: Neuren Pharmaceuticals, Ltd., Auckland (NZ)

( * ) Notice: Subject to any disclaimer, the term of this patent is extended or adjusted under 35 U.S.C. 154(b) by 983 days.

This patent is subject to a terminal disclaimer.

(21) Appl. No.: 11/399,974

(22) Filed: Apr. 7, 2006

(65) Prior Publication Data

US 2006/0258663 A1 Nov. 16, 2006

Related U.S. Application Data

(63) Continuation-in-part of application No. 10/570,395, filed as application No. PCT/US2004/028308 on Aug. 31, 2004.

(60) Provisional application No. 60/499,956, filed on Sep. 3, 2003.

(51) Int. Cl.
| | |
|---|---|
| A01N 43/42 | (2006.01) |
| A01N 43/40 | (2006.01) |
| A61K 31/44 | (2006.01) |
| A61K 31/445 | (2006.01) |
| C07D 221/02 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 211/40 | (2006.01) |

(52) U.S. Cl. .............. 514/299; 514/320; 514/328; 514/413; 546/183; 546/208; 546/219

(58) Field of Classification Search ............. 514/299, 514/320, 328, 413; 546/183, 208, 219
See application file for complete search history.

(56) References Cited

U.S. PATENT DOCUMENTS

2006/0217295 A1 9/2006 Harris et al.

FOREIGN PATENT DOCUMENTS

| WO | WO9940931 | * | 8/1999 |
| WO | WO03041655 | * | 5/2003 |

OTHER PUBLICATIONS

Guttman et. al., Canadian Medical Association Journal, 2003, Canadian Medical Association, vol. 168, pp. 293-301.*
Kostic et. al., Annals of Neurology, 1997, American Neurological Association, vol. 41, pp. 497-504.*
Mann et. al., Journal of Neurology, Neurosurgery, and Psychiatry, 1987, British Medical Association, vol. 50, pp. 341-344.*
Zarkovic, Molecular Aspects of Medicine, 2003, Elsevier Ltd., vol. 24, pp. 293-303.*
U.S. Appl. No. 12/421,871, filed Apr. 10, 2009, Bickerdike.
U.S. Appl. No. 12/002,178, filed Dec. 14, 2007, Paul William Richard Harris.
Int'l Preliminary Report, Apr. 23, 2009.

* cited by examiner

*Primary Examiner*—Sreeni Padmanabhan
*Assistant Examiner*—Sarah Pihonak
(74) *Attorney, Agent, or Firm*—D. Benjamin Borson

(57) ABSTRACT

Embodiments of this invention provide methods for thereapeutic use of cyclic G-2-Allyl Proline to treat disorders of dopaminergic neurons, including Parkinson's disease. Cyclic G-2Allyl P is neuroprotective and has utility as a therapeutic agent for treatment of diseases and other conditions characterised by degeneration and/or death of dopaminergic neurons and the adverse symptoms of such degeneration and/or death. Such symptoms include loss of cognition and motor function. Compounds are also useful for manufacture of medicaments including tablets, capsules and injectable solutions that are useful for treatment of such conditions.

13 Claims, 15 Drawing Sheets

CYCLIC G-2ALLYLPROLINE IN TREATMENT OF PARKINSON'S DISEASE

CLAIM OF PRIORITY

This application is a Continuation-in-Part of U.S. Utility application Ser. No. 10/570,395, filed Mar. 2, 2006 entitled "Neuroprotective Bicyclic Compounds and Methods for Their Use," which is a §371 of PCT International Application PCT/US2004/028308, filed Aug. 31, 2004, Margaret Anne Brimble, Jian Guan and Frank Sieg, Inventors, which claims priority to U.S. Provisional Patent Application Ser. No. 60/499,956 filed Sep. 3, 2003, Margaret Anne Brimble, Jian Guan and Frank Sieg, inventors, titled "Neuroprotective Bicyclic Compounds and Methods for Their Use". Each of the above patent applications is expressly incorporated herein fully by reference.

BACKGROUND

1. Field of the Invention

The present invention relates to novel bicyclic compounds structurally related to diketopiperazines and methods for their therapeutic use. In particular, this invention relates to the neuroprotective activity of such compounds. More particularly, this invention relates to the use of cyclic Glycyl-2-Allyl Proline ("cyclic G-2AllylP" or "cG-2AllylP") and pharmaceutical compositions thereof in the treatment of Parkinson's Disease.

2. Related Art

Degeneration and/or death of cells in the nervous system are major factors in many diseases and medical conditions. Such diseases and conditions include traumatic brain and spinal cord injuries, stroke, neural perfusion secondary to cardiac arterial bypass graft surgery (CABG), Parkinson's disease, Alzheimer's disease, multiple sclerosis, amyotrophic lateral sclerosis and other neurodegenerative diseases. It is of interest to prevent or decrease such cell death and degeneration.

Certain compounds are useful as neuroprotective agents. One such compound is insulin-like growth factor 1 (IGF-1) (Scheepens et al, WO00/13650). IGF-1 is a naturally occurring peptide that can decrease the binding of glutamate to the glutamate receptors of neurons (Bourguinon, U.S. Pat. No. 5,804,550). IGF-1 can also decrease neuronal degradation caused by damage and disease. IGF-1 is cleaved by proteolysis in vivo to give $des_{1-3}$ IGF-1 and the N-terminal tripeptide Gly-Pro-Glu (GPE). GPE and analogues have been found to be neuroprotective (Gluckman et al, U.S. Pat. No. 6,187,906 incorporated herein by reference).

However, such peptides are far from ideal for the treatment of progressive neuronal loss and chronic degeneration especially as they are rapidly metabolised in vivo. There is a need for compounds that provide neuroprotective and neuroregenerative properties and are more metabolically stable especially as regards resistance to proteases.

A derivative of GPE; cyclic Pro-Gly ("cPG"), a diketopiperazine, has been shown to be neuroprotective and neuroregenerative. cPG was found to prevent toxic neural degeneration and cell death and to promote neurite outgrowth in neurons (Guan et al, PCT/US02/36235 incorporated herein by reference). Diketopiperazine analogues of thyrotropin-releasing hormone (TRH) are known to be neuroprotective (Kozikowski et al WO99/40931).

Parkinson's disease is a chronic and progressive motor system disorder. Its symptoms include: tremor, rigidity, bradykinesia, joint and muscle pain due to immobility, poor righting reflexes, dribbling, constipation, postural hypotension or dementia. The cause of the disease is unknown but the symptoms are the consequence of substantial loss of dopaminergic neurons in the pars compacta region of the substantia nigra. In some patients with a history of Parkinson's disease, motor or other symptoms may be episodic, with periods of time that are relatively symptom free, and other periods where symptoms worsen. Thus, there is a need for agents that can be used to reverse adverse symptoms when they occur, and to prevent of decrease the likelihood of appearance of an episode of adverse symptoms.

The main therapy currently used, L-DOPA treatment, is known to cause side-effects such as nausea, vomiting, postural hypotension, confusion or, when the treatment is continued extended periods of time, dyskinesia. Other available therapies including dopamine agonists, anticholinergic drugs, catechol-0-methyl-transferase inhibitors or amantadine, are less effective and also associated with a number of often serious side-effects. There is clearly a need for a therapy, which could help Parkinson's disease sufferers and reduce the number or severity of side-effects in comparison with the available treatment methods.

SUMMARY

We have previously shown in patent application PCT/US2004/02830 filed Aug. 31, 2004, expressly incorporated herein fully by reference, that cyclic GP analogues, including but not limited to cyclic cyclopentyl-G-2MeP and cyclic G-2AllylP are neuroprotective, neuroregenerative and or neuroreparative. We have now discovered that cyclic G-2AllylP is effective in prophylaxis and treatment of Parkinson's disease and its motor symptoms.

Thus, one aspect of this invention provides novel cyclic compounds having the structural formula and substituents described below.

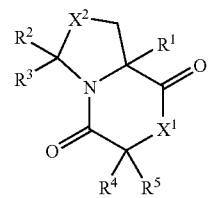

or a pharmaceutically acceptable salt, stereoisomer or hydrate thereof, wherein $R^1$=allyl, $R^2$=$R^3$=$R^4$=$R^5$=H, $X^1$=NH, $X^2$=$CH_2$.

Other aspects of the invention include pharmaceutically acceptable salts of cyclic G-2AllylP.

In still other aspects, this invention includes pharmaceutical compositions comprising a pharmaceutically acceptable excipient and a therapeutically effective amount of cyclic G-2AllylP.

In further aspects, this invention includes methods of treating an animal having a Parkinson's disease comprising administration to that animal an effective amount of a composition comprising cyclic G-2AllylP. In certain other aspects, this invention includes methods for treating an animal with cyclic G-2AllylP in conjunction with at least one other therapeutic agent for the disease being treated. In yet further aspects, the animal to be treated is a human.

BRIEF DESCRIPTION OF THE DRAWINGS

This invention is described with reference to specific embodiments thereof. Other aspects of this invention can be appreciated with reference to the drawings, in which.

DETAILED DESCRIPTION

Definitions

Figure 1:
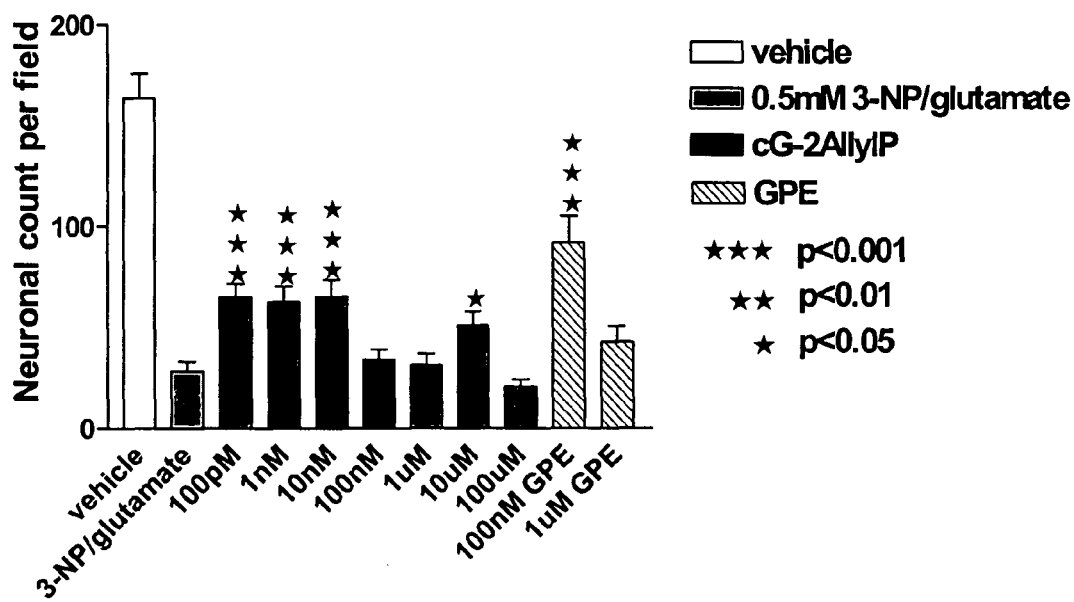
FIG. 1 is a graph showing effects of cyclic G-2AllylP on neuronal survival in animals following excitotoxic oxidative stress.

"Growth factor" refers to an extracellularly active polypeptide that stimulates a cell to grow or proliferate by interacting with a receptor on the cell.

"Injury" includes any acute or chronic damage of an animal that results in degeneration or death of cells in the nervous system. Such cells include neuronal cells and non-neuronal cells. Injury includes stroke, non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, and cerebral trauma. It is to be understood that the above examples are by way of illustration only, and are not intended to be a complete listing of injuries capable of being treated by the compounds and methods of this invention.

A "pharmaceutically acceptable excipient" refers to an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous, and examples of such excipients are included herein.

A "pharmaceutically acceptable salt" refers to a salt that is pharmaceutically acceptable and has the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminium. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid mono-salt or a di-acid salt; and similarly where there are more than two acidic groups present, some or all of such groups can be present as salts.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "stereoisomer" is a molecule having the structure of cyclic G-2-Allyl Proline, but having a chiral center. The term "cyclic G-2-Allyl Proline" includes all stereoisomers.

"Substituted" refers to where one or more of the hydrogen atoms on an alkyl, heteroalkyl, alkenyl, alkynyl, aryl, heteroaryl or arylalkyl radical are independently replaced with another substituent. Substituents include —R', —OR', —SR', —NR'R', —NO$_2$, —CN, —C(O)R', —C(O)OR', —C(O)NR'R', —C(NR')NR'R', —NR'—C(NR')—OR', —NR'—C(NR')—SR', NR'—C(NR')—NR'R', trihalomethyl and halogen where each R' is independently —H, alkyl, heteroalkyl, alkenyl, alkynyl, aryl, arylalkyl, heteroaryl or heteroarylalkyl.

A "therapeutically effective amount" means the amount that, when administered to an animal for treating a disease, is sufficient to effect treatment for a disease or an injury. A "therapeutically effective amount" means an amount that decreases an adverse symptom or finding, promotes a desirable symptom or finding, treats an underlying disorder and/or is curative.

"Treating" or "treatment" of a disease includes inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrole ring, etc.) are omitted from the formulae for clarity, but should be understood to be present.

Compositions of the Invention

Certain embodiments of this invention include a derivative of cPG (cyclic G-2Allyl Proline; cyclic G-2AllylP) having structures as described below.

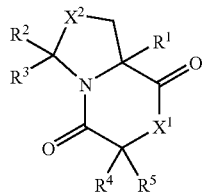

or a pharmaceutically acceptable salt, stereoisomer or hydrate thereof, wherein R$^1$=allyl, R$^2$=R$^3$=R$^4$=R$^5$=H, X$^1$=NH, X$^2$=CH$_2$.

Those with skill in the art will appreciate that the above structural representation can contain chiral centres. The chirality may be either R or S at each centre. The structural drawing can represent only one of the possible tautomeric, diastereomeric or enantiomeric forms, and it should be understood that the invention encompasses any tautomeric, diastereomeric or enantiomeric form, which exhibits biological or pharmacological activity as described herein.

Compositions containing cyclic G-2AllylP may include excipients, adjuvants, binders and/or other substances for manufacturing a pharmaceutically acceptable dosage form. Such dosage forms include suspensions, solutions, tablets, capsules and the like.

Pharmacology and Utility

Certain aspects of this invention include the use of cyclic G-2AllylP in treatment or prevention of cell damage, degeneration and/or death in mammals in response to injury or disease, including Parkinson's disease ("PD"). The pathology of Parkinson's disease is characterized by loss of dopaminergic neurons in the substantia nigra of the brain. There is a useful and art-recognized animal system for studying loss of dopaminergic neurons and Parkinson's disease, namely the use of 6-hydroxydopamine ("6-OHDA"). The unilateral 6-OHDA rat model is one of the most popular experimental models of PD when it comes to the preclinical testing of new symptomatic therapies, neuroprotective strategies (e.g., trophic factor delivery), and transplantation approaches. The molecular alterations caused by 6-OHDA neurotoxicity are comparable to those seen in PD (Bové et al. Toxin-Induced Models of Parkinson's Disease. NeuroRx. July 2005; 2(3): 484-494).

It is well known that treatment of animals with 6-OHDA results in loss of dopaminergic neurons in a pattern very similar to the pattern of cell loss in human beings with Parkinson's disease. Additionally, 6-OHDA treatment produces abnormalities of motor function characteristic of human beings with Parkinson's disease. Further, treatment of animals treated with 6-OHDA and then treated with dopamine replacement therapies (e.g., using L-DOPA) produces clinical improvement in those animals, similar to the therapeutic improvement observed in people with Parkinson's disease. Thus, studies of effects of cyclic G-2AllylP in 6-OHDA-treated animals is reasonably predictive of effects observed in human beings.

Cyclic G-2AllylP can be used in combination with one or more other neuroprotective agents to treat Parkinson's disease. Such other agents may be selected from the group consisting of for example, growth factors and associated derivatives, e.g., insulin-like growth factor-I (IGF-I), insulin-like growth factor-II (IGF-II), the tripeptide GPE, transforming growth factor-β1, activin, growth hormone, nerve growth factor, growth hormone binding protein, and/or IGF-binding proteins. Additional compounds include Glycyl-2-Methyl Prolyl Glutamate and/or other compounds disclosed in U.S. patent application Ser. No. 10/155,864, expressly incorporated herein fully by reference.

Other aspects of the invention include compositions and methods of promoting fasiculation of axons using cyclic G-2AllylP. By promoting formation of nerve bundles, compounds of the invention may be useful in treating conditions in which nerve processes (axons and/or dendrites) have become severed, such as in sharp force injuries, local areas of necrosis or disease, or other localized injuries to nerve processes.

As indicated above, the present invention is broadly based upon the applicant's finding that compounds of the invention including cyclic G-2AllylP can protect cells, particularly nerve cells, against damage, loss of neurites, and/or apoptotic or necrotic cell death.

It is herein demonstrated that cyclic G-2AllylP exhibit neuroprotection in both cell culture and in animal models of acute injury and neurodegenerative disease and can therefore be an effective addition or alternative to conventional therapies for neural degeneration.

Although the mechanism of the protective effects is not known, one possible mechanism involves protecting cells from apoptotic and necrotic cell death. However, regardless of the mechanism of action, compounds of the invention can be used as an effective therapy for a variety of neurological diseases, including hypoxia, ischemia and neurotoxin-induced nerve damage. Moreover, compounds of the invention can be used in the absence of any particular neurological deficit to promote neurite outgrowth and fasiculation of nerves. Thus, in situations in which cell death is not necessarily associated with the neurological disorder (e.g., axonal damage such as caused by spinal cord injury), administration of compounds of the invention may be an effective way of promoting neurite regeneration.

Therapeutic Applications

Compositions and methods of the invention find use in the treatment of animals, such as human patients, suffering from neural injury or disease. Still more generally, the compositions and methods of the invention find use in the treatment of mammals, such as human patients, suffering from nerve damage or potential apoptotic and/or necrotic cell death, due to injuries and diseases.

Specific conditions and diseases characterised by neuronal degeneration, apoptosis and/or necrosis include but are not limited to Alzheimer's disease, Parkinson's disease, multiple sclerosis, amyotrophic lateral sclerosis, spinal muscular atrophy, peripheral neuropathy, Creutzfeldt-Jakob disease, AIDS dementia, progressive supranuclear palsy, myelinopathia centralis diffusa (vanishing white matter disease), chronic neurodegenerative disease, Huntington's disease, stroke, ischemic injury, hypoxic injury, reperfusion injury, head injury, CNS trauma, epilepsy, cerebral ischemia, glaucoma, retinal disorders, optic neuropathy, optic neuritis, Down's syndrome, encephalomyelitis, meningitis, panencephalitis, neuroblastoma, schizophrenia and depression. Each of the above conditions exhibits pathophysiological findings and symptoms that are mimicked by neurotoxicity associated with glutamate toxicity.

Still more generally, the invention has application in the induction of nerve bundle formation following insult in the form of trauma, toxin exposure, asphyxia or hypoxia-ischemia. Additionally, the invention has application in the treatment or prevention of apoptosis in response to injury or disease in the form of cancers, viral infections, autoimmune diseases, neurological diseases and injuries and cardiovascular diseases.

Treatment may be given before an injury, for example, before elective surgery. Examples of relevant elective procedures include neural surgery, in which retraction of lobes of the brain may lead to cerebral oedema, or heart operations, such as valve replacement, in which inevitable small emboli are said to lead to detectable impairment of brain function in some 75% of cases.

Determining Efficacy

The neuroprotective activity of cyclic G-2AllylP of the invention can be measured in vivo using cell counts by methods known to those skilled in the art including the methods of Klempt et al (Klempt et al, 1992, *Molecular Brain Research*: 13: 93-101), microscopic examinations of morphology, cell counts of surviving and dead neurons stained with thionin/fuchsin and the like. Compounds of the invention can also be measured in vitro using mass spectroscopy, immunological, or chromatographic methods known in the art. Herein are disclosed histological techniques suitable for measuring effects in vivo.

CNS damage may for example be measured clinically by the degree of permanent neurological deficit cognitive function, and/or propensity to seizure disorders. As described further herein, adjusted step test may be carried out in non-human animals. Such tests of motor coordination and function are known to correlate with motor function in humans with Parkinson's disease or other neurological disorders. Thus, studies of motor function in rats treated with 6-OHDA are reasonably predictive of motor function in humans with Parkinson's disease. Further, studies of effects of cyclic G-2AllylP using the adjusted step test in rats are reasonably predictive of effects of cyclic G-2AllylP in treating humans with Parkinson's disease.

The therapeutic ratio of a compound is understood to be the ratio of (1) the mean dose that causes adverse side effect over (2) the mean dose that causes a desirable therapeutic effect. Thus, for compounds for which have therapeutic effects at relatively low doses and undesirable side effects at high doses, the therapeutic ratio is >1. Therapeutic ratio can be determined, for example, by comparing the dose that produces significant weight loss (or other observable side-effect) divided by the dose that produces anti-apoptotic and anti-necrotic activity in a suitable in vivo animal species such as the rat or mouse. Suitable animal systems useful for determining therapeutic effects of compounds of this invention include hypoxic-ischemic injury (Sirimanne et al, 1994 *Journal of Neuroscience Methods*: 55: 7-14), experimental immune encephalomyelitis (Mendel et al., 1995 *Eur. J Immunol.*: 25: 1951-1959) and glutamate toxicity.

Pharmaceutical Compositions and Administration

Cyclic G-2AllylP can be administered as part of a medicament or pharmaceutical preparation. This can involve combining a compound of the invention with any pharmaceutically appropriate carrier, adjuvant or excipient. The selection of the carrier, adjuvant or excipient will of course usually be dependent upon the route of administration to be employed.

In general, compounds of this invention will be administered in therapeutically effective amounts by any of the usual modes known in the art, either singly or in combination with other conventional therapeutic agents for the disease being treated. A therapeutically effective amount may vary widely depending on the disease or injury, its severity, the age and relative health of the animal being treated, the potency of the compound(s), and other factors. As an anti-apoptotic and anti-necrotic agent, therapeutically effective amounts of cyclic G-2AllylP may range from 0.001 to 100 milligrams per kilogram mass of the animal, with lower doses such as 0.001 to 0.1 mg/kg being appropriate for administration through the cerebrospinal fluid, such as by intracerebroventricular administration, and higher doses such as 1 to 100 mg/kg being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

Cyclic G-2AllylP may be administered peripherally via any peripheral route known in the art. These can include parenteral routes for example injection into the peripheral circulation, subcutaneous, intraorbital, ophthalmic, intraspinal, intracisternal, topical, infusion (using e.g. slow release devices or minipumps such as osmotic pumps or skin patches), implant, aerosol, inhalation, scarification, intraperitoneal, intracapsular, intramuscular, intranasal, oral, buccal, transdermal, pulmonary, rectal or vaginal. The compositions can be formulated for parenteral administration to humans or other mammals in therapeutically effective amounts (e.g.

amounts which eliminate or reduce the patient's pathological condition) to provide therapy for the neurological diseases described above.

Desirably, cyclic G-2AllylP can be administered orally. The amount of a compound of this invention in the composition may vary widely depending on the type of composition, size of a unit dosage, kind of excipients, and other factors well known to those of ordinary skill in the art. In general, the final composition may comprise from 0.0001 percent by weight (% w) to 10% w of the compound of this invention, preferably 0.001% w to 1% w, with the remainder being the excipient or excipients.

Other convenient administration routes include subcutaneous injection (e.g. dissolved in a physiologically compatible carrier such as 0.9% sodium chloride) or direct administration to the CNS. Using stereotactic devices and accurate maps of an animals' CNS, a compound may be injected directly into a site of neural damage. Such routes of administration may be especially desired in situations in which perfusion of that location is compromised either by decreased vascular perfusion or by decreased cerebral spinal fluid (CSF) flow to that area. Examples include administration by lateral cerebroventricular injection or through a surgically inserted shunt into the lateral cerebroventricle of the brain of the patient, intraveneously, direct injection into the desired location or other routes.

The effective amount of compound in the CNS may be increased by administration of a pro-drug form of a compound, which comprises a compound of the invention and a carrier, where the carrier is joined to a compound of the invention by a linkage, which is susceptible to cleavage or digestion within the patient. Any suitable linkage can be employed which will be cleaved or digested following administration.

However, there is no intention on the part of the applicants to exclude other forms of administration.

In further embodiments of the invention, restoring nerve function in an animal can comprise administering a therapeutic amount of cyclic G-2AllylP in combination with another neuroprotective agent, selected from, for example, growth factors and associated derivatives (insulin-like growth factor-I (IGF-I), insulin-like growth factor-II (IGF-II), transforming growth factor-$\beta$1, glycyl-prolyl-glutamate (GPE), G-2Metehyl Prolyl Glutamate (G-2MePE), activin, growth hormone, nerve growth factor, growth hormone binding protein, IGF-binding proteins (especially IGFBP-3), basic fibroblast growth factor, acidic fibroblast growth factor, the hst/Kfgk gene product, FGF-3, FGF-4, FGF-6, keratinocyte growth factor and androgen-induced growth factor. Additional members of the FGF family include, for example, int-2, fibroblast growth factor homologous factor-1 (FHF-1), FHF-2, FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), $\alpha$-, $\beta$-, $\gamma$-, or consensus interferon, and TNF-$\alpha$. Other forms of neuroprotective therapeutic agents include, for example, clomethiazole; kynurenic acid, Semax, tacrolimus, L-threo-1-phenyl-2-decanoylamino-3-morpholino-1-propanol, andrenocorticotropin-(4-9) analogue (ORG 2766) and dizolcipine (MK-801), selegiline; glutamate antagonists such as, NPS1506, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAdCAM-1 and/or its integrin $\alpha$4 receptors ($\alpha$4$\beta$1 and $\alpha$4$\beta$7), such as anti-MAdCAM-1mAb MECA-367 (ATCC accession no. HB-9478).

Cyclic G-2AllylP is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983, *Biopolymers:* 22: 547-56), poly(2-hydroxyethyl methacrylate) (Langer et al., 1981, *J. Biomed. Mater. Res.:* 15: 267), ethylene vinyl acetate (Langer et al., 1981, *J. Biomed. Mater. Res.:* 15: 267), or poly-D-(-)-3-hydroxybutyric acid (EP 133,988). Sustained-release compositions also include a liposomally entrapped compound. Liposomes containing the compound are prepared by methods known per se: DE 3,218,121, EP 52,322, EP 36,676, EP 88,046, EP 143,949, EP 142,641, Japanese Pat. Appln. 83-118008, U.S. Pat. Nos. 4,485,045 and 4,544,545, and EP 102,324. Ordinarily, the liposomes are of the small (from or about 200 to 800 Angstroms) unilamellar type in which the lipid content is greater than about 30 mol percent cholesterol, the selected proportion being adjusted for the most efficacious therapy.

For parenteral administration, in one embodiment cyclic G-2AllylP is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

Generally, the formulations are prepared by contacting cyclic G-2AllylP uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

A carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

Cyclic G-2AllylP is typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Formulations of cyclic G-2AllylP in pharmaceutical compositions can also include adjuvants. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavouring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a colouring agent, and a flavouring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

For injection, intraventricular administration and other invasive routes of administration, cyclic G-2AllylP must be sterile. Sterility may be accomplished by any method known in the art, for example filtration through sterile filtration membranes (e.g., 0.2 micron membranes). Therapeutic compositions generally are placed into a container having a sterile access port, for example, an intravenous solution bag or vial having a stopper able to be pierced by a hypodermic injection needle.

A pharmaceutical formulation containing cyclic G-2AllylP ordinarily will be stored in unit or multi-dose containers, for example, in sealed ampoules or vials, as an aqueous solution or as a lyophilized formulation for reconstitution. As an example of a lyophilized formulation, 10 mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection. It can be readily appreciated that other dosage forms and types of preparations can be used, and all are considered to be part of this invention.

As described further below, cyclic G-2AllylP can penetrate the CNS after intravenous administration (see Examples 8 and 9). Further, cyclic G-2AllylP can be effectively taken up into the circulation after oral administration (see Example 11). Thus, after oral administration, cyclic G-2AllylP can be taken into the circulation, and from there can enter the CNS, where it can exhibit neuroprotective effects.

Preparation of the Compounds

Starting materials and reagents used in preparing cyclic G-2AllylP are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, 4$^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art.

Starting materials, intermediates, and final products this invention may be isolated and purified using conventional techniques, including filtration, distillation, crystallization, chromatography, and the like. They may be characterized using conventional methods, including physical constants and spectral data.

Cyclic G-2AllylP is a cyclic dipeptide (bicyclic 2,5-diketopiperazine). In general, cyclic G-2AllylP may be prepared by methods such as are already well-known to persons of ordinary skill in the art of peptide and modified peptide synthesis, following the reaction schemes set forth in the Figures following this specification, or by following other methods well-known to those of ordinary skill in the art of the synthesis of peptides and analogues. See for example, Bodanzsky: Principles of Peptide Synthesis, Berlin, New York: Springer-Verlag 1993. Synthesis of the diketopiperazine compounds of this invention may be by solution-phase synthesis as discussed in the Examples or via the solid-phase synthesis method exemplified by Merrifield et al. 1963 *J. Amer. Chem. Soc.*: 85, 2149-2156. Solid phase synthesis may be performed using commercial peptide synthesizers, such as the Applied Biosystems Model 430A, using the protocols established for the instrument.

Specific examples of diketopiperazine synthesis can be found in the Examples following and in, for example, Fischer, 2003, *J. Peptide Science:* 9: 9-35 and references therein. A person of ordinary skill in the art will have no difficulty, taking account of that skill and the knowledge available, and of this disclosure, in developing one or more suitable synthetic methods for compounds of this invention.

The choice of appropriate protecting groups for the method chosen (solid-phase or solution-phase), and of appropriate substrates if solid-phase synthesis is used, will be within the skill of a person of ordinary skill in the art. Appropriate protecting groups for peptide synthesis include t-butyloxycarbonyl (Boc), fluorenylmethyloxycarbonyl (Fmoc), Benzyl (Bzl), t-amyloxycarbonyl (Aoc), tosyl (Tos), benzyloxycarbonyl (Z or Cbz), o-bromo-benzyloxycarbonyl (BrZ) and the like. Additional protecting groups are identified in Merrifield, cited above, as well as in Goodman M. (ed.), "Synthesis of Peptides and Peptidomimetics" in Methods of organic chemistry (Houben-Weyl) (Workbench Edition, E22a,b,c,d,e; 2004; Georg Thieme Verlag, Stuttgart, N.Y.).

The choice of coupling agent for the method chosen will also be within the skill of a person of ordinary skill in the art. Suitable coupling agents include DCC (N,N'-Dicyclohexyl-carbodiimide), Bop (Benzotriazole-1-yl-oxy-tris-(dimethylamino)-phosphonium hexafluorophosphate), PyBop (Benzotriazol-1-yl-oxytripyrrolidinophosphonium hexafluorophosphate), BopCl (bis(2-oxo-3-oxazolidinyl) phosphinic chloride), 2-Chloro-1,3-dimethylimidazolidinium hexafluorophosphate (CIP) and the like. Other compounds may be used in the synthesis e.g. to prevent racemisation, such as HOBt (N-Hydroxybenzotriazole) and HOAt (1-Hydroxy-7-azabenzotriazole).

For example, cyclic G-2AllylP may be synthesized by the following methods.

Scheme 1:

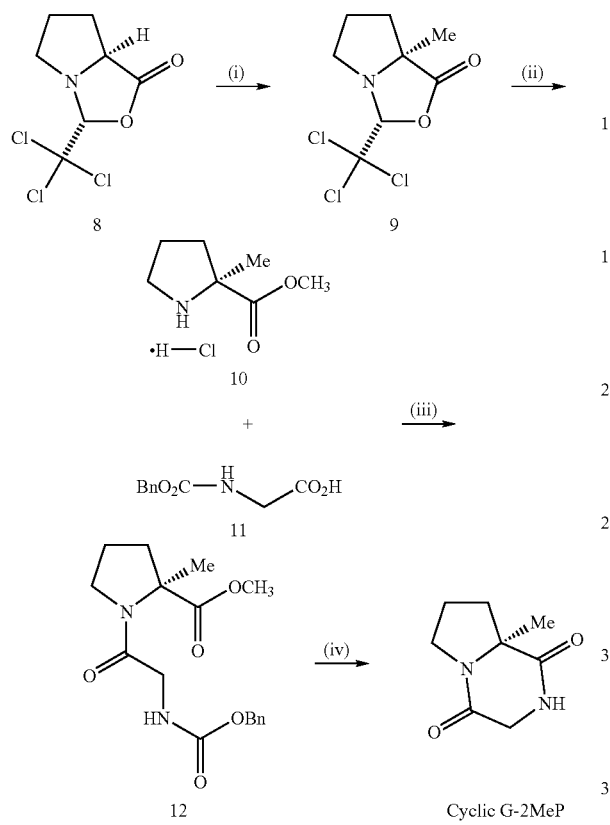

Reagents, conditions and yields: (i) LDA, THF, -78° C., iodomethane, -78 -> -50° C., 2 h (63%); (ii) SOCl₂, CH₃OH, reflux, N₂, 2.5 h (98%); (iii) Et₃N, BoPCl, CH₂Cl₂, RT, N₂, 20.5 h (78%); (iv) 10% Pd/C, CH₃OH, RT, 15 h (98%).

Oxazolidinone 8 can be synthesized by reaction of chloral with proline. This oxazolidinone can then reduced using lithium diisopropylamide (LDA), followed by addition of a methyl group using iodomethane to produce oxazolidinone 9. Thionyl chloride or acetyl chloride can be used to produce the methyl ester of 2-methyl proline as in Scheme 1 above. It will be apparent to those skilled in the art that the iodomethane can be replaced with a suitable halogen compound to produce various analogues modified at the carbon 2 position. For example, use of iodoethane will produce 2-ethylproline; use of allylbromide will produce 2-allylproline and use of benzylbromide will produce 2-benzylproline.

The proline protected at the C-terminus can then be coupled to an amino acid protected at the N-terminal with a suitable protecting group such as Cbz, Boc or Fmoc. Suitable coupling reagents for this procedure will be apparent to those skilled in the art and include such reagents as bis(2-oxo-3-oxazolidinyl)phosphinic chloride (BoPCl), dicyclohexylcarbodiimide (DCC), 2-Chloro-1,3-dimethylimidazolidinium hexafluorophosphate (CIP) (Babu and Ananda, 2001, *Indian J. Chem. Sect. B.,*: 40B(1): 70; Akaji and Aimoto 2001, *Tetrahedron,* 57(9), 1749). The dipeptide thus formed can then be selectively de-protected at the N-terminus, using for example, hydrogenation to remove Cbz groups and trifluoroacetic acid (TFA) to remove Boc groups. The molecule then cyclises with elimination of the methoxy group of the methyl ester to give the diketopiperazine.

The amino acid used in scheme 1 is glycine which gives compounds of formula 1 where $R^4=R^5=H$. Replacement of glycine with other amino acids will result in compounds of formula 1 where $R^4=H$ and $R^5$ is equivalent to the side chain of the respective amino acid with the appropriate stereochemistry.

Scheme 2:

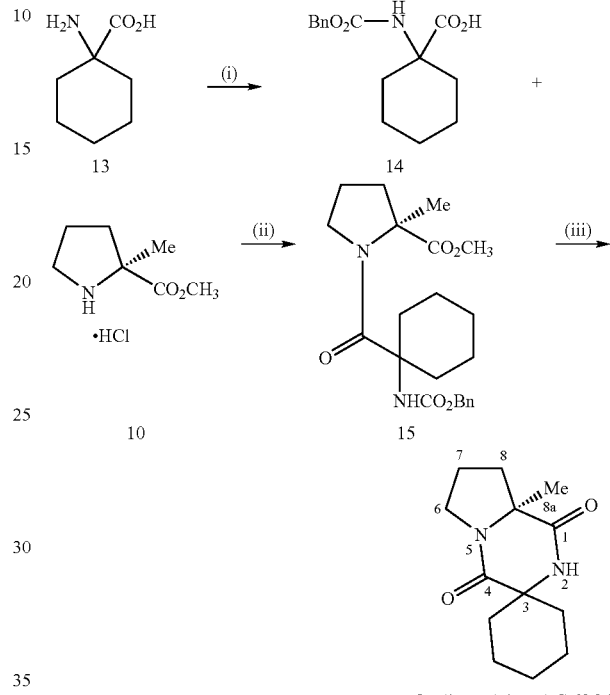

Reagents, conditions and yields: (i) BnO₂CCl, Na₂CO₃, H₂O-dioxane (3:1), 19 h, 96%; (ii) Et₃N, HOAt, CIP, 1,2-dichloroethane, reflux, N₂, 19 h (23%); (iii) 10% Pd/C, CH₃OH, RT, 17 h (65%).

1-Aminocyclohexanecarboxylic acid 13 (Fluka) can be protected at the N-terminus using a protecting group such as Cbz. This compound can then be coupled to a proline derivative suitably protected at the C-terminus using an appropriate coupling agent such as 2-chloro-1,3-dimethylimidazolidinium hexafluorophosphate (CIP) as in Scheme 2. The dipeptide thus formed can then be selectively de-protected at the N-terminus via hydrogenation for example, and the resultant elimination of the methoxy group of the methyl ester produces the diketopiperazine. It will be apparent to those skilled in the art that replacement of the 1-aminocyclohexanecarboxylic acid with analogous compounds such as 1-aminocyclopentanecarboxylic acid or 1-aminocyclopropanecarboxylic acid will be possible. It will also be apparent that the methyl group at the C-2 position of proline may be replaced with other substituents such as ethyl, allyl and benzyl as discussed above leading to modification at C-8a in the diketopiperazine structure (illustrated in Scheme 2).

All patent and literature references cited throughout the specification are expressly incorporated by reference in their entirety as if each had been separately so incorporated.

EXAMPLES

The present invention is further illustrated by the following examples. These examples are offered by way of illustration only and are not intended to limit the scope of the invention.

15

General Methods

Flash chromatography was performed using Scharlau 60 (40-60 μm mesh) silica gel. Analytical thin layer chromatography was carried out on 0.20 mm pre-coated silica gel plates (ALUGRAM® SIL G/UV$_{254}$) and compounds visualized using UV fluorescence, or heating of plates dipped in potassium permanganate in alkaline solution.

Melting points in degrees Celsius (° C.) were determined on an Electrothermal® melting point apparatus and are uncorrected.

Optical rotations were measured at 20° C. on a Perkin Elmer 341 polarimeter using 10 cm path length cells and are given in units of $10^{-1}$ degcm$^2$g$^{-1}$. Samples were prepared in the solvent indicated at the concentration specified (measured in g/100 cm$^3$). IR spectra were recorded on a Perkin Elmer Spectrum One FT-IR spectrometer. The samples were prepared as thin films on sodium chloride discs or as solids in potassium bromide discs. A broad signal indicated by br. The frequencies (υ) as absorption maxima are given in wavenumbers (cm$^{-1}$).

NMR spectra were recorded on a Bruker AVANCE DRX400 ($^1$H, 400 MHz; $^{13}$C, 100 MHz) or a Bruker AVANCE 300 ($^1$H, 300 MHz; $^{13}$C, 75 MHz) spectrometer at ambient temperatures. For $^1$H NMR data chemical shifts are described in parts per million downfield from SiMe$_4$ and are reported consecutively as position ($\delta_H$), relative integral, multiplicity (s=singlet, d=doublet, t=triplet, dd=doublet of doublets, m=multiplet, br=broad), coupling constant (J/Hz) and assignment. For $^{13}$C NMR data, chemical shifts are described in parts per million relative to CDCl$_3$ and are reported consecutively as position ($\delta_C$), degree of hybridization as determined by DEPT experiments, and assignment. $^1$H NMR spectra were referenced internally using SiMe$_4$ (δ 0.00) or CDCl$_3$ (δ 7.26). $^{13}$C NMR spectra were referenced internally using CDCl$_3$ (δ 77.0). When two sets of peaks arise in the NMR spectra due to different conformations around the glycine-proline amide bond, the chemical shift for the minor cis conformer is marked with an asterisk (*).

Accurate mass measurements were recorded on a VG-70SE mass spectrometer.

Hexane and dichloromethane were distilled prior to use. Methanol was dried using magnesium turnings and iodine, and distilled under nitrogen. Triethylamine was dried over calcium hydride and distilled under nitrogen.

Example 1

Synthesis of (8aS)-Methyl-hexahydropyrrolo[1,2-a]pyrazine-1,4-dione (Cyclic G-2MeP)

Scheme 1:

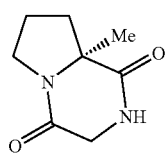

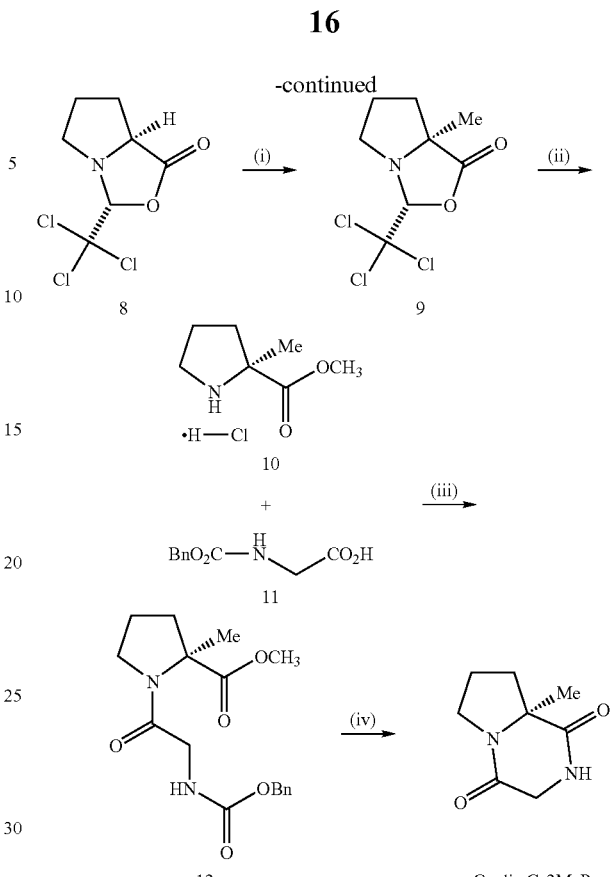

Reagents, conditions and yields: (i) LDA, THF, -78° C., iodomethane, -78 -> -50° C., 2 h (63%); (ii) SOCl$_2$, CH$_3$OH, reflux, N$_2$, 2.5 h (98%); (iii) Et$_3$N, BoPCl, CH$_2$Cl$_2$, RT, N$_2$, 20.5 h (78%); (iv) 10% Pd/C, CH$_3$OH, RT, 15 h (98%).

(2R,5S)-4-Methyl-2-trichloromethyl-1-aza-3-oxabicyclo[3.3.0]octan-4-one 9 n-BuLi (1.31 M, 4.68 cm$^3$, 6.14 mmol) was added dropwise to a stirred solution of diisopropylamine (0.86 cm$^3$, 6.14 mmol) in dry tetrahydrofuran (10 cm$^3$) at -78° C. under an atmosphere of nitrogen. The solution was stirred for 5 min, warmed to 0° C. and stirred for 15 min. The solution was then added dropwise to a solution of oxazolidinone 8 (1.00 g, 4.09 mmol) in dry tetrahydrofuran (20 cm$^3$) at -78° C. over 20 min (turned to a dark brown colour), stirred for a further 30 min then iodomethane (0.76 cm$^3$, 12.3 mmol) was added dropwise over 5 min. The solution was warmed to -50° C. over 2 h. Water (15 cm$^3$) was added and the solution warmed to room temperature and extracted with chloroform (3×40 cm$^3$). The combined organic extracts were dried (MgSO$_4$), filtered and evaporated to dryness in vacuo to give a dark brown semi-solid. Purification of the residue by flash column chromatography (15% ethyl acetate-hexane) afforded oxazolidinone 9 (0.67 g, 63%) as a pale yellow solid: mp 55-57° C. (lit., 57-60° C.); $\delta_H$ (300 MHz, CDCl$_3$) 1.53 (3H, s, CH$_3$), 1.72-2.02 (3H, m, Proβ-H and Proγ-H$_2$), 2.18-2.26 (1H, m, Proβ-H), 3.15-3.22 (1H, m, Proβ-H), 3.35-3.44 (1H, m, Proδ-H) and 4.99 (1H, s, NCH).

Methyl L-2-methylprolinate hydrochloride 10 a) Using Acetyl Chloride

Oxazolidinone 9 (0.60 g, 2.33 mmol) was dissolved in dry methanol (15 cm$^3$) under an atmosphere of nitrogen and acetyl chloride (0.33 cm³, 4.66 mmol) was added dropwise to the ice-cooled solution. The solution was heated under reflux for 4.5 h, then the solvent removed under reduced pressure to give a brown oil which was purified by flash column chromatography (10% CH₃OH—CH₂Cl₂) affording the hydrochloride 10 (0.2 g, 48%) as a flaky white solid: mp 107-109° C. (lit., 106-108° C.); $\delta_H$ (300 MHz, CDCl₃) 1.81 (3H, s, CH₃), 1.93-2.14 (3H, m, Proβ-$H_AH_B$ and Proγ-$H_2$), 2.33-2.39 (1H, m, Proβ-$H_AH_B$), 3.52-3.56 (2H, m, Proδ-$H_2$) and 3.82 (3H, s, CO₂CH₃).

b) Using Thionyl Chloride

An ice-cooled solution of oxazolidinone 9 (53 mg, 0.21 mmol) in dry methanol (1 cm³) was treated dropwise with thionyl chloride (0.045 cm³, 0.62 mmol). The solution was heated under reflux for 2.5 h, cooled and the solvent removed under reduced pressure to yield a brown oil. The oil was dissolved in toluene (5 cm³), concentrated to dryness to remove residual thionyl chloride and methanol then purified by flash column chromatography (10% CH₃OH—CH₂Cl₂) to afford the hydrochloride 10 (16 mg, 43%) as a flaky white solid. The ¹H NMR assignments were in agreement with those reported above.

Methyl-N-benzyloxycarbonyl-glycyl-L-2-methylprolinate 12

Dry triethylamine (0.27 cm³, 1.96 mmol) was added dropwise to a solution of hydrochloride 10 (0.11 g, 0.61 mmol) and N-benzyloxycarbonyl-glycine 11 (98.5%) (0.17 g, 0.79 mmol) in dry dichloromethane (35 cm³) under an atmosphere of nitrogen at room temperature, and the reaction mixture stirred for 10 min. Bis(2-oxo-3-oxazolidinyl)phosphinic chloride (BoPCl, 97%) (0.196 g, 0.77 mmol) was added and the resultant colourless solution was stirred for 20.5 h. The solution was washed successively with 10% aqueous hydrochloric acid (30 cm³) and saturated aqueous sodium hydrogen carbonate (30 cm³), dried (MgSO₄), filtered and evaporated to dryness in vacuo. Purification of the resultant residue by flash column chromatography (50-80% ethyl acetate-hexane; gradient elution) yielded dipeptide 12 (0.18 g, 92%) as a colourless oil. Amide 12 was shown to exist as a 98:2 trans:cis mixture of conformers by ¹³C NMR analysis (the ratio was estimated from the relative intensities of the resonances at δ 20.8 and 23.5 assigned to the Proγ-C atoms of the minor and major conformers, respectively): $[\alpha]_D$ −33.0 (c 1.0 in MeOH); $\nu_{max}$ (film)/cm⁻¹ 3406, 2952, 1732, 1651, 1521, 1434, 1373, 1329, 1310, 1284, 1257, 1220, 1195, 1172, 1135, 1107, 1082, 1052, 1029, 986, 965, 907, 876, 829, 775, 738 and 699; $\delta_H$ (300 MHz, CDCl₃) 1.49 (3H, s, CH₃), 1.77-2.11 (4H, m, Proβ-$H_2$ and Proγ-$H_2$), 3.43-3.48 (2H, m, Proδ-$H_2$), 3.61 (3H, s, OCH₃), 3.85-3.89 (2H, m, Glyα-$H_2$), 5.04 (2H, s, PhCH₂), 5.76 (1H, br s, N—H) and 7.21-7.28 (5H, s, ArH); $\delta_C$ (75 MHz, CDCl₃) 13.8* (CH₃, Proα-CH₃), 21.1 (CH₃, Proα-CH₃), 20.8* (CH₂, Proγ-C), 23.5 (CH₂, Proγ-C), 38.0 (CH₂, Proβ-C), 40.8* (CH₂, Proβ-C), 43.3 (CH₂, Glyα-C), 45.5* (CH₂, Glyα-C), 46.6 (CH₂, Proδ-C), 48.7* (CH₂, Proδ-C), 51.9* (CH₃, OCH₃), 52.1 (CH₃, OCH₃), 60.0* (quat., Proα-C), 66.0 (quat., Proα-C), 66.3 (CH₂, PhCH₂), 68.6* (CH₂, PhCH₂), 127.5 (CH, Ph), 127.6 (CH, Ph), 127.9* (CH, Ph), 128.1 (CH, Ph), 128.3* (CH, Ph), 136.2 (quat., Ph), 155.9 (quat., NCO), 166.0 (quat., Gly-CON), 169.4* (quat., Gly-CON) and 173.6 (quat., CO₂CH₃); m/z (EI+) 334.1535 (M⁺. C₁₇H₂₂N₂O₅ requires 334.1529).

(8aS)-Methyl-hexahydropyrrolo[1,2-a]pyrazine-1,4-dione (Cyclic G-2MeP)

To a solution of dipeptide 12 (0.167 g, 0.51 mmol) in methanol (8.0 cm³) was added 10% Pd on activated charcoal (8.1 mg, 0.076 mmol) and the vessel flushed with hydrogen gas. The resulting suspension was stirred vigorously under an atmosphere of hydrogen for 15 h. The mixture was then filtered through a Celite pad then a short plug of silica gel with methanol, and the solvent removed under reduced pressure to produce cyclic G-2MeP (83 mg, 98%) as a yellow solid: mp 133-135° C.; $[\alpha]_D$ −128.1 (c 0.52 in MeOH); $\delta_H$ (300 MHz, CDCl₃) 1.36 (3H, s, CH₃), 1.87-2.01 (3H, m, Proβ-$H_AH_B$ and Proγ-$H_2$), 2.07-2.21 (1H, m, Proβ-$H_AH_B$), 3.45-3.64 (2H, m, Proδ-$H_2$), 3.82 (1H, dd, J 17.1 and 4.1, $CH_AH_B$NH), 3.99 (1H, d, J 17.1, $CH_AH_B$NH) and 7.66 (1H, br s, N—H); $\delta_C$ (75 MHz, CDCl₃) 20.2 (CH₂, Proγ-C), 23.2 (CH₃, Proα-CH₃), 35.0 (CH₂, Proβ-C), 44.7 (CH₂, Proδ-C), 45.9 (CH₂, CH₂NH), 63.8 (quat., Proα-C), 163.3 (quat., NCO) and 173.3 (quat., CONH); m/z (EI+) 168.08986 (M⁺. C₈H₁₂N₂O₂ requires 168.08988).

Example 2

Synthesis of (8aS)-Methyl-spiro[cyclohexane-1,3 (4H) tetrahydropyrrolo[1,2-a]pyrazine]-1,4(2H)-dione (Cyclic cyclohexyl-G-2MeP)

Scheme 2:

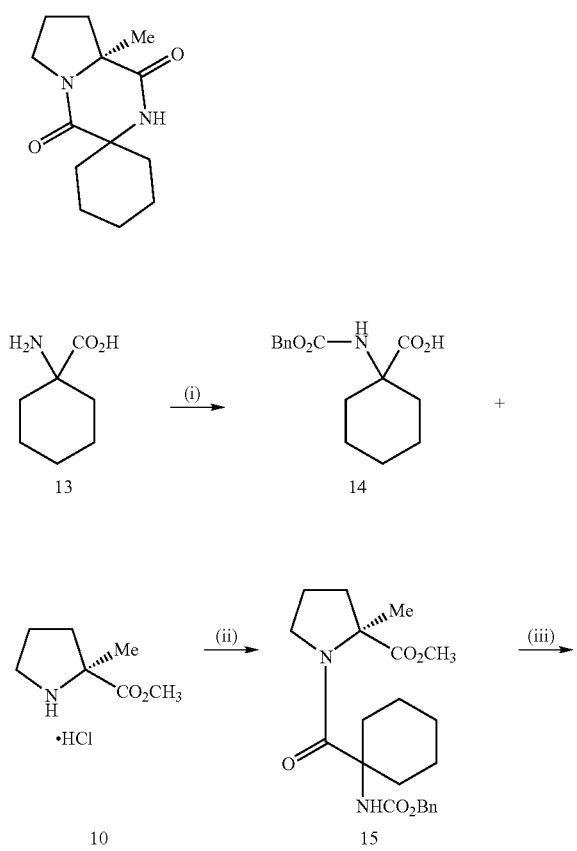

-continued

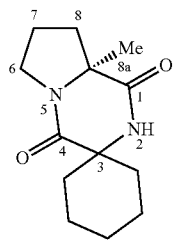

Cyclic cyclohexyl-G-2MeP

Reagents, conditions and yields: (i) BnO₂CCl, Na₂CO₃, H₂O-dioxane (3:1), 19 h, 96%; (ii) Et₃N, HOAt, CIP, 1,2-dichloroethane, reflux, N₂, 19 h (23%); (iii) 10% Pd/C, CH₃OH, RT, 17 h (65%).

N-Benzyloxycarbonyl-1-aminocyclohexane-1-carboxylic acid (14)

To a suspension of 1-aminocyclohexanecarboxylic acid 13 (0.72 g, 5.02 mmol) and sodium carbonate (1.6 g, 15.1 mmol) were dissolved in water-dioxane (21 cm$^3$, 3:1) was added benzyl chloroformate (0.79 cm$^3$, 5.52 mmol) was added dropwise and the solution was stirred at room temperature for 19.5 h. The aqueous layer was washed with diethyl ether (60 cm$^3$), acidified with 2 M HCl and extracted with ethyl acetate (2×60 cm$^3$). The organic layers were combined, dried (MgSO$_4$), filtered and evaporated under reduced pressure to produce a colourless oil, which solidified on standing to crude carbamate 14 (1.23 g, 88%) as a white solid: mp 152-154° C. (lit., 148-150° C.); $\delta_H$ (400 MHz, CDCl$_3$) 1.27-1.56 (3H, m, 3×cyclohexyl-H), 1.59-1.73 (3H, m, 3×cyclohexyl-H), 1.85-1.91 (2H, m, 2×cyclopentyl-H), 2.05-2.09 (2H, m, 2×cyclopentyl-H), 5.02 (1H, br s, N—H), 5.12 (2H, s, OCH$_2$Ph) and 7.27-7.36 (5H, s, Ph); $\delta_C$ (100 MHz, CDCl$_3$) 21.1 (CH$_2$, 2×cyclohexyl-C), 25.1 (CH$_2$, 2×cyclohexyl-C), 32.3 (CH$_2$, cyclohexyl-C), 59.0 (quat., 1-C), 67.1 (CH$_2$, OCH$_2$Ph), 128.1 (CH, Ph), 128.2 (CH, Ph), 128.5 (CH, Ph), 136.1 (quat., Ph), 155.7 (quat., NCO$_2$) and 178.7 (quat., CO$_2$H).

Methyl-N-benzyloxycarbonyl-cyclohexyl-glycyl-L-2-methylprolinate (15)

Dry triethylamine (0.21 cm$^3$, 1.5 mmol) was added dropwise to a solution of hydrochloride 10 (84.0 mg, 0.47 mmol), carboxylic acid 14 (0.17 g, 0.61 mmol) and 1-hydroxy-7-azabenzotriazole (16 mg, 0.12 mmol) in dry 1,2-dichloroethane (26 cm$^3$) under an atmosphere of nitrogen at room temperature, and the reaction mixture stirred for 10 min. 2-Chloro-1,3-dimethylimidazolidinium hexafluorophosphate (0.13 g, 0.47 mmol) was added and the resultant solution heated under reflux for 21 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (40-50% ethyl acetate-hexane; gradient elution) yielded amide 15 (16 mg, 9%) as a white solid. Amide 15 was shown to exist as a 11:1 trans:cis mixture of conformers by $^{13}$C NMR analysis (the ratio was estimated from the relative intensities of the resonances at δ 41.3 and 48.2 assigned to the Proδ-C atoms of the minor and major conformers, respectively): mp 219-222° C.; [α]$_D$ −44.9 (c 1.31 in CH$_2$Cl$_2$); ν$_{max}$ (film)/cm$^-$ 3239, 2927, 1736, 1707, 1617, 1530, 1450, 1403, 1371, 1281, 1241, 1208, 1194, 1165, 1150, 1132, 1089, 1071, 1028, 984, 912, 796, 749, 739 and 699; $\delta_H$ (400 MHz, CDCl$_3$) 1.24-2.10 (17H, m, Proα-CH$_3$, Proβ-H$_2$, Proγ-H$_2$ and 5×cyclohexyl-H$_2$), 3.25-3.48 (1H, br m, Proδ-H$_A$H$_B$), 3.61-3.87 (4H, br m, OCH$_3$ and Proδ-H$_A$H$_B$), 4.92-5.19 (3H, m, N—H and OCH$_2$Ph) and 7.35-7.37 (5H, s, Ph); $\delta_C$ (100 MHz, CDCl$_3$) 21.26 (CH$_2$, cyclohexyl-C), 21.33 (CH$_2$, cyclohexyl-C), 21.7 (CH$_3$, Proα-CH$_3$), 24.8 (CH$_2$, cyclohexyl-C), 25.0 (CH$_2$, Proγ-C), 29.4* (CH$_2$, cyclohexyl-C), 29.7* (CH$_2$, cyclohexyl-C), 31.1 (CH$_2$, cyclohexyl-C), 31.6 (CH$_2$, cyclohexyl-C), 31.9* (CH$_2$, cyclohexyl-C), 32.2* (CH$_2$, cyclohexyl-C), 32.8* (CH$_2$, cyclohexyl-C), 37.3 (CH$_2$, Proβ-C), 41.4* (CH$_2$, Proδ-C), 48.2 (CH$_2$, Proδ-C), 52.1 (CH$_3$, OCH$_3$), 59.1 (quat., Glyα-C), 66.7 (CH$_2$, OCH$_2$Ph), 67.3* (CH$_2$, OCH$_2$Ph), 67.4 (quat. Proα-C), 128.0* (CH, Ph), 128.1* (CH, Ph), 128.3 (CH, Ph), 128.5 (CH, Ph), 128.7 (CH, Ph), 136.6 (quat., Ph), 153.7 (quat., NCO$_2$), 171.0 (quat., Gly-CO) and 174.8 (quat., CO$_2$CH$_3$); m/z (EI+) 402.2151 (M$^+$. C$_{22}$H$_{30}$N$_2$O$_5$ requires 402.2155).

(8aS)-Methyl-spiro[cyclohexane-1,3(4H)-tetrahydropyrrolo[1,2-a]pyrazine]-1,4(2H)-dione (Cyclic cyclohexyl-G-2MeP)

To a solution of amide 15 (40 mg, 0.01 mmol) in methanol (3.3 cm$^3$) was added 10% Pd on activated charcoal (1.6 mg, 0.015 mmol) and the vessel flushed with hydrogen gas. The resulting suspension was stirred vigorously under an atmosphere of hydrogen for 61.5 h, then filtered through a Celite™ pad with methanol (15 cm$^3$). The filtrate was concentrated to dryness under reduced pressure to produce a yellow semi-solid which was purified by reverse-phase C18 flash column chromatography (0-10% CH$_3$CN/H$_2$O; gradient elution) to produce cyclic cyclohexyl-G-2MeP (19 mg, 81%) as a white solid: mp 174-177° C.; [α]$_D$ −63.8 (c 1.13 in CH$_2$Cl$_2$); ν$_{max}$ (film)/cm$^{-1}$ 3215, 2925, 2854, 1667, 1646, 1463, 1427, 1276, 1232, 1171, 1085, 1014, 900, 868, 818, 783, 726 and 715; $\delta_H$ (400 MHz, CDCl$_3$) 1.31-1.89 (12H, m, 9×cyclohexyl-H and 8a-CH$_3$), 1.94-2.15 (4H, m, 7-H$_2$ and 8-H$_2$), 2.26 (1H, td, J 13.7 and 4.5, 1×cyclohexyl-H), 3.44-3.51 (1H, m, 6-H$_A$H$_B$), 3.79-3.86 (1H, m, 6-H$_A$H$_B$) and 6.40 (1H, br s, N—H); $\delta_C$ (100 MHz, CDCl$_3$) 19.5 (CH$_2$, 7-C), 20.6 (CH$_2$, cyclohexyl-C), 20.8 (CH$_2$, cyclohexyl-C), 24.5 (CH$_2$, cyclohexyl-C), 25.0 (CH$_3$, 8a-CH$_3$), 33.7 (CH$_2$, cyclohexyl-C), 36.3 (CH$_2$, 8-C), 36.5 (CH$_2$, cyclohexyl-C), 44.7 (CH$_2$, 6-C), 59.5 (quat., 8a-C), 64.0 (quat., 3-C), 168.1 (quat., 4-C) and 171.6 (quat., 1-C); m/z (EI+) 236.15246 (M$^+$. C$_{13}$H$_{20}$N$_2$O$_2$ requires 236.15248).

Example 3

Synthesis of (8aS)-Allyl-hexahydropyrrolo[1,2-a]pyrazine-1,4-dione (Cyclic G-2AllylP)

Scheme 3:

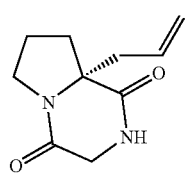

-continued

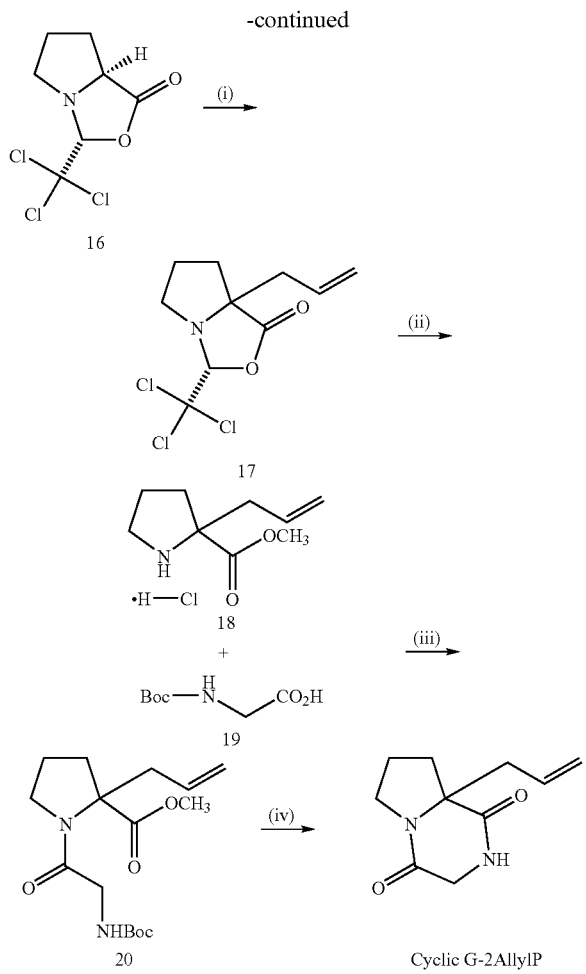

Reagents, conditions and yields: (i) LDA, THF, −78° C., allyl bromide, −78 -> −30° C., N₂, 4 h (60%); (ii) acetyl chloride, CH₃OH, reflux, N₂, 24 h (63%); (iii) Et₃N, BoPCl, CH₂Cl₂, RT, N₂, 19.5 h (45%); (iv) TFA, CH₂Cl₂, 1 h, then Et₃N, CH₂Cl₂, 23 h (37%).

(2R,5S)-4-Allyl-2-trichloromethyl-1-aza-3-oxabicyclo[3.3.0]octan-4-one 17 n-BuLi (1.31 M, 9.93 cm³, 13.0 mmol) was added dropwise to a stirred solution of diisopropylamine (1.82 cm³, 13.0 mmol) in dry tetrahydrofuran (20 cm³) at −78° C. under an atmosphere of nitrogen. The solution was stirred for 5 min, warmed to 0° C., stirred for 15 min then added dropwise to a solution of pro-oxazolidinone 16 (2.12 g, 8.68 mmol) in dry tetrahydrofuran (40 cm³) at −78° C. over 20 min and the reaction mixture was stirred for a further 30 min then allyl bromide (2.25 cm³, 26.0 mmol) was added dropwise over 5 min. The solution was warmed slowly to −30° C. over 4 h, quenched with H₂O (30 cm³) and the mixture warmed to room temperature and extracted with chloroform (3×80 cm³). The combined organic extracts were dried (MgSO₄), filtered and evaporated to dryness in vacuo to produce a dark brown semi-solid which was purified by flash column chromatography (10-20% ethyl acetate-hexane; gradient elution) to produce oxazolidinone 17 (1.48 g, 60%) as an orange oil which solidified at 0° C., for which the nmr data were in agreement with that reported in the literature: $\delta_H$ (400 MHz, CDCl₃) 1.58-1.92 (2H, m, Proγ-H₂), 1.96-2.14 (2H, m, Proβ-H₂), 2.50-2.63 (2H, m, Proδ-H₂), 3.12-3.23 (2H, m, CH₂—CH=CH₂), 4.97 (1H, s, NCH), 5.13-5.18 (2H, m, CH=CH₂) and 5.82-5.92 (1H, m, CH=CH₂); $\delta_C$ (100 MHz, CDCl₃) 25.1 (CH₂, Proγ-C), 35.1 (CH₂, Proβ-C), 41.5 (CH₂, Proδ-C), 58.3 (CH₂, CH₂CH=CH₂), 71.2 (quat., Proα-C), 100.4 (quat., CCl₃), 102.3 (CH, NCH), 119.8 (CH₂, CH₂CH=CH₂), 131.9 (CH, CH₂CH=CH₂) and 176.1 (quat., C=O); m/z (CI+) 284.0009 [(M+H)⁺. C₁₀H₁₃³⁵Cl₃NO₂ requires 284.0012], 285.9980 [(M+H)⁺. C₁₀H₁₃³⁵Cl₂³⁷ClNO₂ requires 285.9982], 287.9951 [(M+H)⁺. C₁₀H₁₃³⁵Cl³⁷Cl₂NO₂ requires 287.9953] and 289.9932 [(M+H)⁺. C₁₀H₁₃³⁷Cl₃NO₂ requires 289.9923].

Methyl L-2-allylprolinate hydrochloride 18

An ice-cooled solution of oxazolidinone 17 (0.64 g, 2.24 mmol) in dry methanol (15 cm³) was treated dropwise with a solution of acetyl chloride (0.36 cm³, 5.0 mmol) in methanol (5 cm³). The solution was heated under reflux for 24 h, then cooled and the solvent removed under reduced pressure. The resultant brown oil was dissolved in toluene (40 cm³) and concentrated to dryness to remove residual thionyl chloride and methanol, then purified by flash column chromatography (5-10% CH₃OH—CH₂Cl₂; gradient elution) to afford hydrochloride 18 (0.29 g, 63%) as a green solid for which the NMR data were in agreement with that reported in the literature: $\delta_H$ (300 MHz, CDCl₃) 1.72-2.25 (3H, m, Proβ-H$_A$H$_B$ and Proγ-H₂), 2.32-2.52 (1H, m, Proβ-H$_A$H$_B$), 2.72-3.10 (2H, m, Proδ-H₂), 3.31-3.78 (2H, m, CH₂CH=CH₂), 3.84 (3H, s, CO₂CH₃), 5.20-5.33 (2H, m, CH=CH₂), 5.75-5.98 (1H, m, CH=CH₂) and 8.06 (1H, br s, N—H); m/z (CI+) 170.1183 [(M+H)⁺. C₉H₁₆NO₂ requires 170.1181].

Methyl N-tert-butyloxycarbonyl-glycyl-L-2-allylprolinate 20

Dry triethylamine (0.28 cm³, 2.02 mmol) was added dropwise to a solution of hydrochloride 18 (0.13 g, 0.63 mmol) and N-tert-butyloxycarbonyl-glycine 19 (0.14 g, 0.82 mmol) in dry dichloromethane (35 cm³) under an atmosphere of nitrogen at room temperature, and the reaction mixture was stirred for 10 min. Bis(2-oxo-3-oxazolidinyl)phosphinic chloride (BoPCl, 97%) (0.20 g, 0.80 mmol) was added and the solution stirred for 19.5 h, then washed successively with 10% aqueous hydrochloric acid (35 cm³) and saturated aqueous sodium hydrogen carbonate (35 cm³), dried (MgSO₄), filtered and evaporated to dryness in vacuo. Purification of the resultant residue by flash column chromatography (40% ethyl acetate-hexane) yielded dipeptide 20 (0.09 g, 45%) as a light yellow oil: [α]$_D$ +33.8 (c 0.83 in CH₂Cl₂); $v_{max}$ (film)/cm⁻¹ 3419, 3075, 2977, 2930, 2874, 1739, 1715, 1656, 1499, 1434, 1392, 1366, 1332, 1268, 1248, 1212, 1168, 1122, 1051, 1026, 1003, 943, 919, 867, 830, 779, 739, 699 and 679; $\delta_H$ (300 MHz, CDCl₃) 1.42 [9H, s, C(CH₃)₃], 1.93-2.08 (4H, m, Proβ-H₂ and Proγ-H₂), 2.59-2.67 (1H, m, CH$_A$H$_B$CH=CH₂), 3.09-3.16 (1H, m, CH$_A$H$_B$CH=CH₂), 3.35-3.44 (1H, m, Proδ-H$_A$H$_B$), 3.56-3.62 (1H, m, Proδ-H$_A$H$_B$), 3.70 (3H, s, OCH₃), 3.89 (2H, d, J 4.2, Glyα-H₂), 5.06-5.11 (2H, m, CH=CH₂), 5.42 (1H, br s, Gly-NH) and 5.58-5.72 (1H, m, CH=CH₂); $\delta_C$ (75 MHz, CDCl₃) 23.7 (CH₂, Proγ-C), 28.3 [CH₃, C(CH₃)₃], 35.0 (CH₂, Proβ-C), 37.6 (CH₂, CH₂CH=CH₂), 43.3 (CH₂, Glyα-C), 47.5 (CH₂, Proδ-C), 52.5 (CH₃, OCH₃), 68.8 (quat., Proα-C), 79.5 [quat., C(CH₃)₃], 119.4 (CH₂, CH=CH₂), 132.9 (CH, CH=CH₂), 155.7 (quat., NCO₂), 166.9 (quat., Gly-CON) and 173.8 (quat., CO₂CH₃); m/z (EI+) 326.1845 (M⁺. C₁₆H₂₆N₂O₅ requires 326.1842).

(8aS)-Allyl-hexahydropyrrolo[1,2-a]pyrazine-1,4-dione (Cyclic G-2AllylP)

To a solution of dipeptide 20 (0.09 g, 0.28 mmol) in dichloromethane (9 cm$^3$) at room temperature was added trifluoroacetic acid (1 cm$^3$, 0.013 mmol) dropwise and the reaction mixture was stirred for 1 h under an atmosphere of nitrogen. The solution was evaporated under reduced pressure to give a colorless oil which was dissolved in dichloromethane (10 cm$^3$), dry triethylamine (0.096 cm$^3$, 0.69 mmol) was added and the reaction mixture stirred for 4.5 h, after which further triethylamine (0.096 cm$^3$, 0.69 mmol) was added. The reaction mixture was stirred overnight, concentrated to dryness to give a green oil which was purified by flash column chromatography (10% CH$_3$OH—CH$_2$Cl$_2$) to produce cyclic G-2AllylP (20 mg, 37%) as an off-white solid: mp 106-109° C.; $[\alpha]_D$ –102.7 (c 0.95 in CH$_2$Cl$_2$); $\nu_{max}$ (CH$_2$Cl$_2$)/cm$^{-1}$ 3456, 3226, 2920, 1666, 1454, 1325, 1306, 1299, 1210, 1133, 1109, 1028, 1010, 949, 928, 882, 793, 761 and 733; $\delta_H$ (400 MHz, CDCl$_3$) 1.92-2.01 (2H, m, Proγ-H$_2$), 2.09-2.16 (2H, m, Proβ-H$_2$), 2.39-2.56 (2H, m, CH$_2$CH=CH$_2$), 3.46-3.53 (1H, m, Proδ-H$_A$H$_B$), 3.78-3.87 (2H, m, Proδ-H$_A$H$_B$ and Glyα-H$_A$H$_B$), 4.09 (1H, d, J 17.2, Glyα-H$_A$H$_B$), 5.16-5.20 (2H, m, CH=CH$_2$), 5.73-5.84 (1H, m, CH=CH$_2$) and 7.17 (1H, br s, N—H); $\delta_C$ (100 MHz, CDCl$_3$) 20.1 (CH$_2$, Proγ-C), 34.1 (CH$_2$, Proβ-C), 41.7 (CH$_2$, CH$_2$CH=CH$_2$), 44.9 (CH$_2$, Proδ-C), 46.4 (CH$_2$, Glyα-C), 67.2 (quat., Proα-C), 120.9 (CH$_2$, CH=CH$_2$), 131.0 (CH, CH=CH$_2$), 163.4 (quat., NCO) and 171.7 (quat., CONH); m/z (EI+) 195.1132 (M$^+$. C$_{10}$H$_{15}$N$_2$O$_2$ requires 195.1134).

Example 4

Synthesis of (8aS)-Methyl-spiro[cyclopentane-1,3(4H)-tetrahydropyrrolo[1,2-a]pyrazine]-1,4(2H)-dione (Cyclic Cyclopentyl-G-2MeP)

Scheme 4:

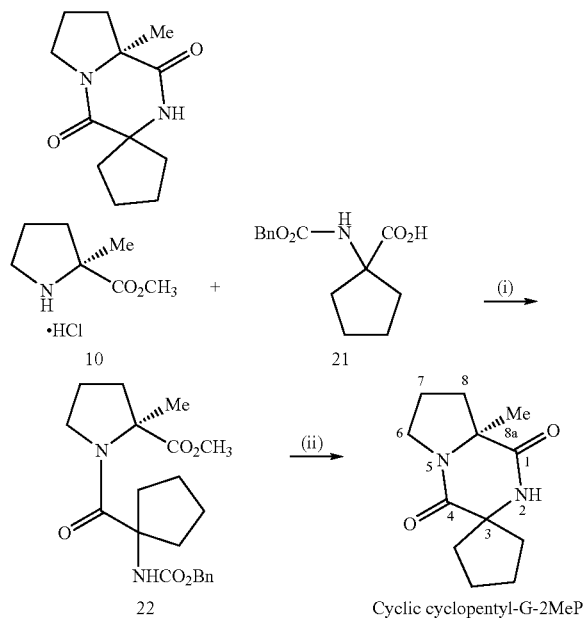

Reagents, conditions and yields: (i) Et$_3$N, HOAt, CIP, 1,2-dichloroethane, 83° C., N$_2$, 19 h (23%); (ii) 10% Pd/C, CH$_3$OH, RT, 17 h (65%).

N-Benzyloxycarbonyl-1-aminocyclopentane-1-carboxylic acid 21

A solution of benzyl chloroformate (0.290 g, 1.1 mmol) in dioxane (2.5 cm$^3$) was added dropwise to a solution of 1-aminocyclopentanecarboxylic acid (Fluka) (0.2 g, 1.54 mmol) and sodium carbonate (0.490 g, 4.64 mmol) in water (5 cm$^3$) at 0° C. Stirring was continued at room temperature overnight and the reaction mixture washed with ether. The aqueous layer was acidified with 2M hydrochloric acid, extracted with ethyl acetate, dried (Na$_2$SO$_4$), filtered and the solvent removed to afford carbamate 21 (0.253 g, 62%) as an oil which solidified on standing. Carbamate 21 was shown to be a 70:30 mixture of conformers by $^1$H NMR analysis (the ratio was estimated from the integration of the resonances at δ 5.31 and 7.29-7.40, assigned to the N—H protons of the major and minor conformers, respectively): mp 70-80° C. (lit.[1] 82-86° C., ethyl acetate, petroleum ether); $\delta_H$ (400 MHz; CDCl$_3$; Me$_4$Si) 1.83 (4H, br s, 2×cyclopentyl-H$_2$), 2.04 (2H, br s, cyclopentyl-H$_2$), 2.20-2.40 (2H, m, cyclopentyl-H$_2$), 5.13 (2H, br s, OCH$_2$Ph), 5.31 (0.7H, br s, N—H) and 7.29-7.40 (5.3H, m, Ph and N—H*); $\delta_C$ (100 MHz; CDCl$_3$) 24.6 (CH$_2$, cyclopentyl-C), 37.5 (CH$_2$, cyclopentyl-C), 66.0 (quat., cyclopentyl-C), 66.8 (CH$_2$, OCH$_2$Ph), 128.0 (CH, Ph), 128.1 (CH, Ph), 128.4 (CH, Ph), 136.1 (quat, Ph), 155.8 (quat., NCO$_2$) and 179.5 (quat., CO$_2$H).

*denotes resonance assigned to minor conformer.

Methyl N-benzyloxycarbonyl cyclopentyl-glycyl-L-2-methylprolinate 22

Dry triethylamine (0.19 cm$^3$, 1.4 mmol) was added dropwise to a solution of hydrochloride 10 (78 mg, 0.43 mmol), carboxylic acid 21 (0.15 g, 0.56 mmol) and 1-hydroxy-7-azabenzotriazole (Acros) (15 mg, 0.11 mmol) in dry 1,2-dichloroethane (24 cm$^3$) under an atmosphere of nitrogen at room temperature, and the reaction mixture stirred for 10 min. 2-Chloro-1,3-dimethylimidazolidinium hexafluorophosphate (CIP) (Aldrich) (0.12 g, 0.43 mmol) was added and the resultant solution heated under reflux for 19 h, then washed successively with 10% aqueous hydrochloric acid (30 cm$^3$) and saturated aqueous sodium hydrogen carbonate (30 cm$^3$), dried (MgSO$_4$), filtered and evaporated to dryness in vacuo. Purification of the resultant residue by flash column chromatography (60% ethyl acetate-hexane) yielded amide 22 (39 mg, 23%) as a white solid. Amide 22 was shown to exist as a 3:1 trans:cis mixture of carbamate conformers by $^{13}$C NMR analysis (the ratio was estimated from the relative intensities of the resonances at δ 154.1 and 155.7 assigned to the carbamate carbonyl-C atoms of the major and minor conformers, respectively): mp 200-203° C.; $[\alpha]_D$ –54.5 (c 1.52 in CH$_2$Cl$_2$); $\nu_{max}$ (film)/cm$^{-1}$ 3432, 3239, 3042, 2953, 1736, 1712, 1627, 1540, 1455, 1417, 1439, 1374, 1282, 1256, 1216, 1194, 1171, 1156, 1136, 1100, 1081, 1042, 1020, 107, 953, 917, 876, 756 and 701; $\delta_H$ (400 MHz, CDCl$_3$) 1.33-1.53 (3H, br m, Proα-CH$_3$), 1.62-2.20 (11H, m, Proβ-H$_2$, Proγ-H$_2$ and 7×cyclopentyl-H), 2.59-2.71 (1H, br m, 1×cyclopentyl-H), 3.31-3.42 (1H, br m, Proδ-H$_A$H$_B$), 3.58-3.79 (4H, br m, OCH$_3$ and Proδ-H$_A$H$_B$), 4.92-5.17 (3H, m, N—H and OCH$_2$Ph) and 7.27-7.42 (5H, s, Ph); $\delta_C$ (100 MHz, CDCl$_3$) 21.7 (CH$_3$, Proα-CH$_3$), 24.1* (CH$_2$, cyclopentyl-C), 24.2 (CH$_2$, cyclopentyl-C), 24.4 (CH$_2$, Proγ-C), 24.5 (CH$_2$, cyclopentyl-C), 36.4 (CH$_2$, cyclopentyl-C), 37.1 (CH$_2$, cyclopentyl-C), 37.2* (CH$_2$, cyclopentyl-C), 37.7 (CH$_2$, Proβ-C), 38.2* (CH$_2$, cyclopentyl-C), 48.5 (CH$_2$, Proδ-C), 52.1 (CH$_3$, OCH$_3$), 66.6 (CH$_2$, OCH$_2$Ph), 66.9 (quat., Proα-C), 67.2 (quat., Glyα-C), 127.8 (CH, Ph), 128.2 (CH, Ph), 128.4 (CH, Ph), 136.6 (quat., Ph), 154.1 (quat., NCO$_2$), 155.7* (quat., NCO$_2$), 170.5 (quat., Gly-CO) and 174.7 (quat., CO$_2$CH$_3$); m/z (EI+) 388.1991 (M$^+$. C$_{21}$H$_{28}$N$_2$O$_5$ requires 388.1998).

(8aS)-Methyl-spiro[cyclopentane-1,3(4H)-tetrahydropyrrolo[1,2-a]pyrazine]-1,4(2H)-dione (Cyclic cyclopentyl-G-2MeP)

To a solution of amide 22 (54 mg, 0.14 mmol) in methanol (4.6 cm$^3$) was added 10% Pd on activated charcoal (2.2 mg, 0.021 mmol) and the vessel flushed with hydrogen gas. The resulting suspension was stirred vigorously under an atmosphere of hydrogen for 17 h, then filtered through a Celite™ pad with methanol (15 cm$^3$). The filtrate was concentrated to dryness under reduced pressure to give a yellow semi-solid which was purified by reverse-phase C18 flash column chromatography (0-10% CH$_3$CN/H$_2$O; gradient elution) to produce cyclic cyclopentyl-G-2MeP (20 mg, 65%) as a yellow solid: mp 160-163° C.; [α]$_D$ –97.9 (c 1.61 in CH$_2$Cl$_2$); ν$_{max}$ (film)/cm$^{-1}$ 3429, 2956, 2928, 2856, 1667, 1643, 1463, 1432, 1373, 1339, 1254, 1224, 1175, 1086, 1048, 976, 835, 774 and 730; δ$_H$ (300 MHz, CDCl$_3$) 1.47 (3H, br s, 8a-CH$_3$), 1.56-2.19 (11H, m, 8-H$_2$, 7-H$_2$ and 7×cyclopentyl), 2.58-2.67 (1H, br m, 1×cyclopentyl), 3.48-3.56 (1H, m, 6-H$_A$H$_B$), 3.72-3.82 (1H, m, 6-H$_A$H$_B$) and 6.56 (1H, br s, N—H); δ$_C$ (75 MHz, CDCl$_3$) 19.9 (CH$_2$, 7-C), 24.6 (CH$_2$, cyclopentyl), 24.92 (CH$_3$, 8a-CH$_3$), 24.93 (CH$_2$, cyclopentyl), 36.0 (CH$_2$, 8-C), 38.7 (CH$_2$, cyclopentyl), 41.9 (CH$_2$, cyclopentyl), 44.8 (CH$_2$, 6-C), 64.3 (quat., 8a-C), 66.8 (quat., 3-C), 168.3 (quat., 4-C) and 172.2 (quat., 1-C); m/z (EI+) 222.1369 (M$^+$. C$_{12}$H$_{18}$N$_2$O$_2$ requires 222.1368).

In Vitro and In Vivo Testing

The following pharmacological studies demonstrate neuroprotective features of cyclic G-2AllylP. They are not intended to be limiting, and other compositions and methods of this invention can be developed without undue experimentation. All of those compositions and methods are considered to be part of this invention. All the following experiments were carried out using protocols developed under guidelines approved by the University of Auckland Animal Ethics Committee.

Example 5

Effects of Cyclic G-2AllylP and Cyclic Cyclopentyl-G-2MeP on Cerebellar Cell Explants To determine the effects of cG-2AllylP and cyclic cyclopentyl-G-2MeP on neuronal cells in vitro, a series of studies was carried out using cerebellar explants from adult rats. In vitro systems are suitable for studying neuronal proliferation, neurite growth, formation of nerve bundles and effects of toxins on neural cells, effects that parallel effects observed in vivo. Thus, results of studies using in vitro cerebellar explants are predictive of effects of interventions in vivo.

In a first series of studies, effects of glutamate on cerebellar explants were determined. At physiological concentrations, glutamate is a neurotransmitter in the CNS of mammals, including humans. However, at sufficiently high concentrations, glutamate is neurotoxic, resulting in neuronal cell death. Because glutamate is a naturally occurring neurotransmitter in the CNS of mammals, including humans, and because glutamate neurotoxicity is recognized in the art as reflective of neurotoxicity in general, and including cell death and degeneration, it is a valuable tool useful for identifying and characterizing agents effective in treatment of neurodegeneration and neural cell death.

Materials and Methods

Cover slips were placed into a large Petri dish and washed in 70% alcohol for 5 minutes, then washed with Millipore H$_2$O. The cover slips were air dried, and coated with Poly-D-Lysine (1 mg/ml stock solution in PBS, 90-100 μl) for 2 hours at 34° C.

Extraction of Cerebellar Tissue

Postnatal day 8 Wistar rats were used for the study. The rats were sacrificed and placed in ice for 1 minute, decapitated and the cerebellum removed and placed on ice. Cerebellum tissue was placed in 1 ml of 0.65% glucose-supplemented PBS (10 μl 65% stock D (+)glucose/1 ml PBS) in a large Petri dish, chopped up into smaller sections and triturated with a 1 ml insulin syringe via a 23 G (0.4 mm) needle, and then squirted back into the glucose solution in the large Petri dish. The tissue was sieved through (125 μm pore size gauze) and centrifuged (2 minutes at 60 g) twice to exchange the medium into serum-free BSA-supplemented START V medium (Biochrom, Germany). The second centrifugation step was done with 1 ml of START V medium. The microexplants were reconstituted into 500 μl of START V medium and put on ice.

Cultivation of Cerebellar Cells

Two hours after PDL-coating, the slides were washed with Millipore H$_2$O and air dried. Each slide was placed into a small Petri dish (diameter: 35 mm) and 40 μl of START V/cell suspension was added. The tissue was incubated for 2 hours at 34° C. (settlement period). START V-medium (1 ml) was then added to the Petri dish and cultivated at 34° C. in the presence of 5% CO$_2$ in air at 100% humidity for 48 hours.

Drug Application

For the study, certain explant cultures were exposed to vehicle (PBS) only. In the first study (Study 1) 10 μl of toxin 1 (L-glutamate—100 mM in Millipore water; final concentration: 1 mM) and 10 μl of toxin 2 (3-nitropropionic acid—50mM-pH 7—in Millipore water, final concentration: 0.5 mM) was applied simultaneously with the drug to be tested (10 mM stock solution prepared in PBS and diluted to final concentrations between 1-100 nM). In each case, the drugs were left in contact with the explants for the duration of the study.

Methods for Determining Drug Effects

After explants were exposed to drugs for the study period, cells were then rinsed in PBS and then fixed in increasing concentrations of paraformaldehyde (500 μl of 0.4% PFA was applied; then 1.2% PFA; then 3% PFA and finally 4% PFA (each fixation step: 2-3 minutes). Finally, the microexplants were rinsed in PBS.

Neurons in the explants were then evaluated for morphology (presence of neurites) and counted as live cells per microscopic field. Four fields displaying highest cell density were counted per cover slip and the data presented as mean±standard error of the mean (SEM); n=4 each. Statistical significance was evaluated by using the non-paired Student's t-test.

Results

Cyclic G-2-AllylP

The results of the study are shown in FIG. 1. Glutamate treatment (1 mM; filled bar) resulted in about an 85% loss of cerebellar neurons having neurites compared to vehicle-treated controls (open bar). In contrast, cG-2AllylP significantly increased the numbers of cells having neurites in a dose-dependent manner when administered simultaneously with glutamate (shaded bars). Treatment with low doses of cG-2AllylP (100 pM to 10 nm) showed a significant decrease in glutamate-induced neurotoxicity; the recovery from injury between 25.5% to 27.3%. Treatment with 100 nM of GPE resulted in 47.1% recovery.

Cyclic cyclopentyl-G-2MeP

Figure 2:
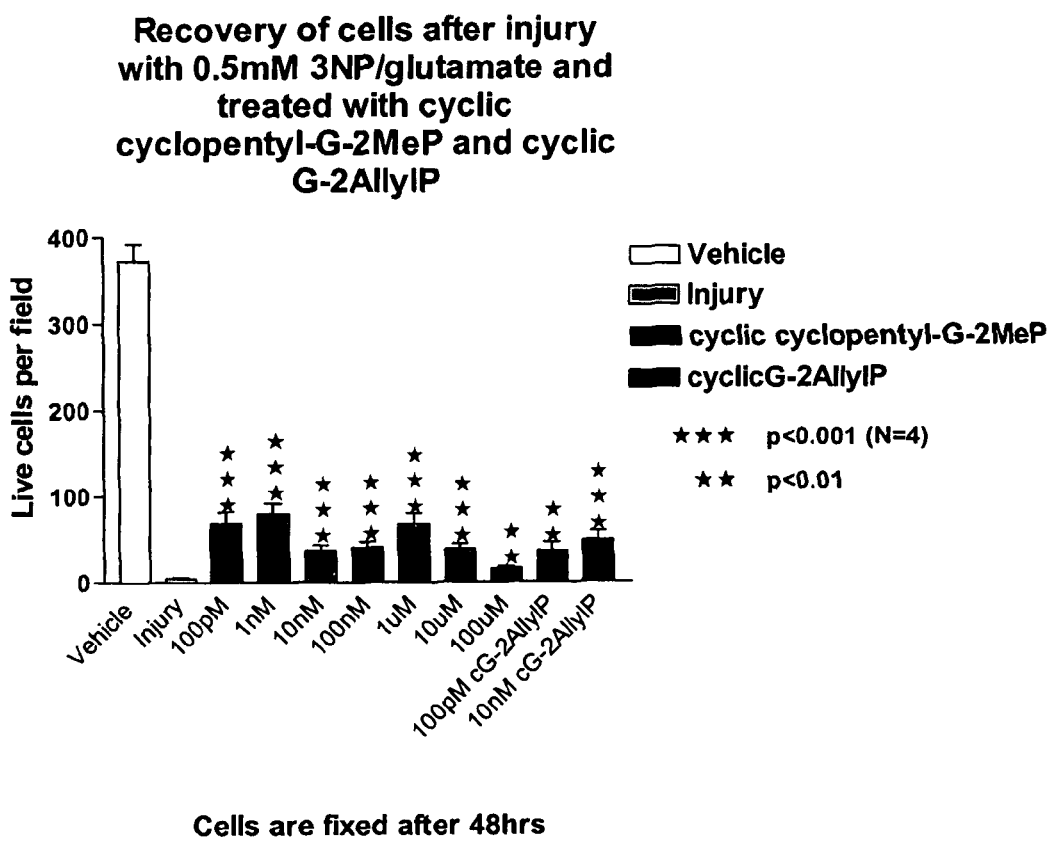
FIG. 2 is a graph showing effects of cyclic cyclopentylG-2MeP on neuronal survival in animals following excitotoxic oxidative stress.

The results of the study are shown in FIG. 2. Cyclic cyclopentyl-G-2MeP significantly increased the number of cells having neurites when simultaneously administered with glutamate (light shaded bars). Treatment with low doses of cyclic cyclopentyl-G-2MeP showed a significant decrease in glutamate-induced neurotoxicity.

Conclusions

Both cG-2AllylP and cyclic cyclopentyl-G-2MeP independently decreased or prevented glutamate-induced neurotoxicity, indicating that both drugs are neuroprotective and can be used to inhibit neuronal degeneration or cell death.

Example 6

Effects of cG-2AllylP on Hypoxic-Ischemic Injury I

Materials and Methods

To determine whether cG-2AllylP might prevent neuronal injury in response to stroke, cardiac arterial bypass graft surgery (CABG) or other hypoxic insults, a series of studies were carried out in rats that had been exposed to hypoxic-ischemic injury (HI). Adult rats (Wistar, 280-310 g, male) were used. The modified Levine model preparation and experimental procedures were used (Rice et al, 1981, *Ann. Neurol.:* 9: 131-141; Guan et al *J.,* 1993, *Cereb. Blood Flow Metab.:* 13(4): 609-16). These procedures in brief, consist of an HI injury induced by unilateral carotid artery ligation followed by inhalational asphyxia in the animals with an implanted lateral ventricular cannula. A guide cannula was stereotaxically placed on the top of the dura 1.5 mm to the right of the mid-line and 7.5 mm anterior to the interaural zero plane under halothane anaesthesia. The right carotid artery was double ligated two days after the cannulation. After 1 hour recovery from the anaesthesia, each of the rats were placed in an incubator where the humidity (90±5%) and temperature (31°±0.5° C.) were controlled for another hour, then exposed to hypoxia (6% oxygen) for 10 min. The animals were kept in the incubator for an additional 2 hours before treatment.

Nine pairs of rats were treated intracerebral ventricularly (icv) with either cG-2AllylP (2 ng) or its vehicle (normal saline) 2 hours after hypoxic-ischemic insult. Rats in each group were simultaneously infused with cG-2AllylP or its vehicle under light anaesthesia (1.5% halothane) 2 hours after the insult. A total volume of 20 µl was infused (icv) over 20 minutes controlled by a micro-infusion pump.

Histological examination was performed on rats 5 days after the hypoxic-ischemic injury. The rats were killed with an overdose of sodium pentobarbital and the brains were perfused transcardially with normal saline followed by 10% formalin. The brains were kept in the same fixative for a minimum of 2 days before being processed using a standard paraffin imbedding procedure.

Coronal sections 6 µm in thickness were cut from the striatum, cerebral cortex and hippocampus and were stained with thionin and acid fuchsin. The histological outcome was assessed at three levels: (1) the mid level of the striatum, (2) where the completed hippocampus first appeared and (3) the level where the ventral horn of the hippocampus just appears. The severity of tissue damage was scored in the striatum, cortex and the CA1/2, CA3, CA4 and dentate gyrus of the hippocampus. Tissue damage was identified as neuronal loss (acidophilic (red) cytoplasm and contracted nuclei), pan-necrosis and cellular reactions. Tissue damage was scored using the following scoring system: 0: tissue showed no tissue damage, 1: <5% tissue was damaged, 2: <50% tissue was damaged, 3: >50% tissue was damaged and 4: >95% tissue was damaged.

Results and Conclusion

Figure 3:
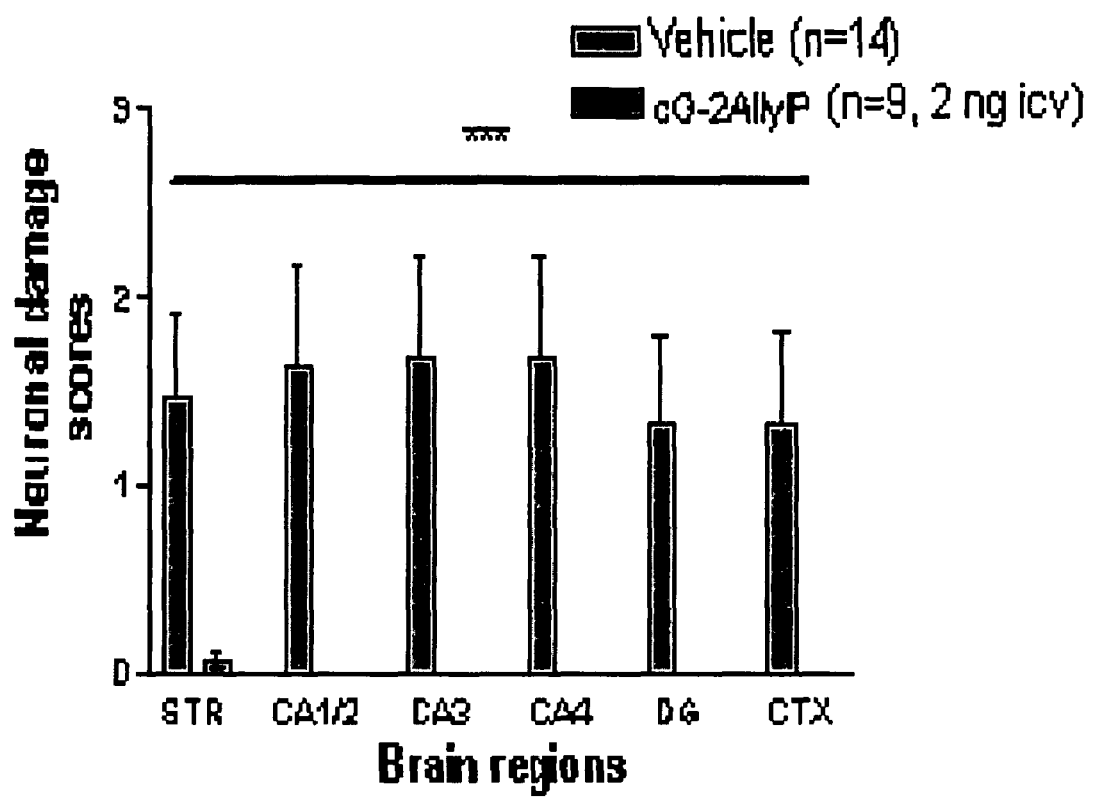
FIG. 3 is a graph showing the neuroprotective effects of cyclic G-2AllylP in animals subjected to global brain ischemia.

The results of this study are shown in FIG. 3. FIG. 3 shows that hypoxic-ischemic injury (light grey bars of each set) resulted in significant damage scores in each brain regions of the ipsilateral hemisphere studied. FIG. 3 also shows that central administration of a relatively low dose of cG-2AllylP (darker grey bars of each set; 2 ng) significantly reduced the tissue damage in each brain region examined compared to the vehicle treated group (p<0.001).

It can be seen that cG-2AllylP can be neuroprotective against neural damage caused by hypoxic-ischemic injury, even when administered after hypoxic-ischemic injury. This surprising finding indicates that cG-2AllylP is a useful agent to treat a variety of conditions characterized by neural degeneration or cell death.

Example 7

Effects of cG-2AllylP on Hypoxic-Ischemic Injury II

Materials and Methods

Materials and methods described in Example 6 were used and the number of treatment groups was increased. Rats were divided into 5 treatment groups treated intracerebral ventricularly (icv) with one of 4 doses of cG-2AllylP or with its vehicle (normal saline) 2 hours after hypoxic-ischemic insult (1: n=10, 2 ng; 2: n=9, 4 ng; 3: n=9, 20 ng; 4: n=10, 100 ng; and 5: n=9, vehicle).

Figure 4:
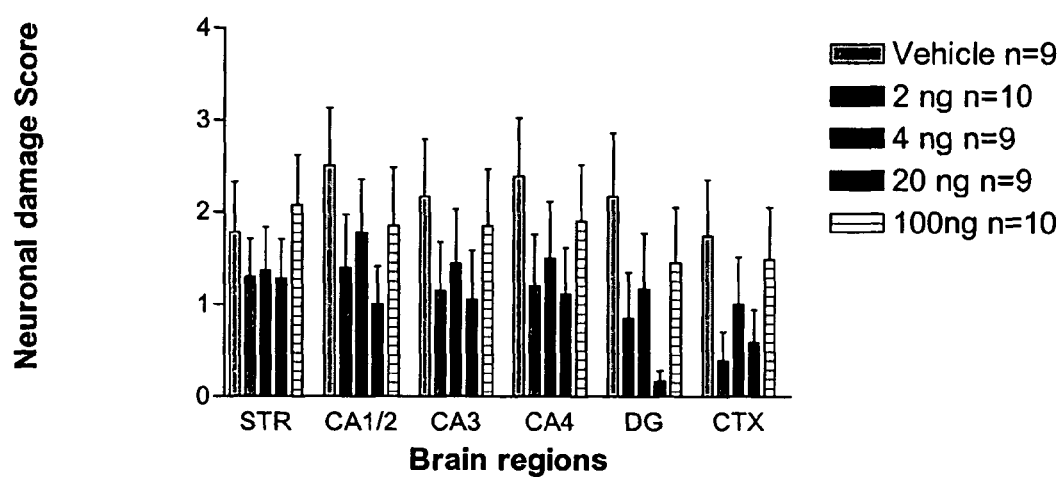
FIG. 4 is a graph showing effects of different doses of cyclic G-2AllylP on neuroprotection in animals subjected to global brain ischemia.

FIG. 4 shows hypoxia alone (vehicle) produces neuronal damage scores in all areas of the brain studied. In animals treated with cG-2AllylP, hypoxia had less effect, even though the agent was administered after the hypoxic/ischemic injury. The neuroprotective effect was observed for all doses of cG-2AllylP, except for the highest dose (100 ng) administered to the lateral ventricle. However, in all other sites and with all other doses, cG-2AllylP lessened the neural damage effects of hypoxia/ischemia. Moreover, cG-2AllylP had an increased efficacy in brain regions that experienced progressive injury associated with delayed cell death, such as that associated with apoptosis. In brain regions such as the dentate gyrus and the cerebral cortex, that are more resistant to HI injury, the progression of injury is known to be slower and more severe than in the brain regions that are more sensitive to HI injury such as the striatum and the CA1/2, CA3 and CA4 subregions of the hippocampus. This result shows that cG-2AllylP can be beneficial in treatment of chronic neurological disorders.

The descriptions and examples provided herein are for purposes of illustration only. The scope of this invention to is not intended to be limited to the described embodiments. Other embodiments incorporating elements of the invention can be practiced without undue experimentation by persons of ordinary skill in the art. All such embodiments are therefore considered to be part of this invention. All references cited herein are incorporated fully by reference.

Example 8

Effects of cG-2AllylP on Cell Proliferation in the Hippocampus after HI Injury Methods and Materials The studies were approved by the animal Ethics Committee of the University of Auckland. Cyclic G-2AllylP was synthesised as described above and dissolved in normal saline before the treatment. Male 50-60 days old Wistar rats weighing between 280-300 g were used.

Experimental Procedures

Animals were assigned to one of 3 groups: 1. normal (n=6), 2. HI+vehicle (n=12) and 3. HI+cG-2AllylP (n=13). Animals in group 2 and 3 were subjected to an HI insult described in Example 6 and then were treated intracerebroventricularly (icv) with either 66 ng/kg of cG-2AllylP or its vehicle (normal saline) given at 2 hours after hypoxic-ischemic insult. The surgery and procedures for the intracerebroventricular administration have been described elsewhere (Guan et al. 1993 *Journal of Cerebral blood Flow & Metabolism* 13: 609-616). Under a light anaesthesia (1.5% halothane) the rats in those groups were simultaneously infused with cG-2AllylP or its vehicle using a micro-infusion pump.

5 days after the hypoxic-ischemic injury histological examination was performed on rats in all 3 groups. The rats were killed with an overdose of sodium pentobarbital and were perfused transcardially with normal saline followed by 10% formalin. The brains were kept in the same fixative for a minimum of 2 days before being processed using a standard paraffin embedding procedure.

The immunohistochemical staining of PCNA, GFAP and isolectin B-4 was performed. The number of PCNA positive cells was counted in (a) the SVZ and (b) in the CA1/2, CA3, CA4 and dentate gyrus areas of the hippocampus. The GFAP ad isolectin B-4 positive cells were counted in CA1/2 and CA4 subregions of hippocampus. In each case the number of cells was then averaged as cells/mm depending on the length of the wall used for counting.

Results

Figure 5:
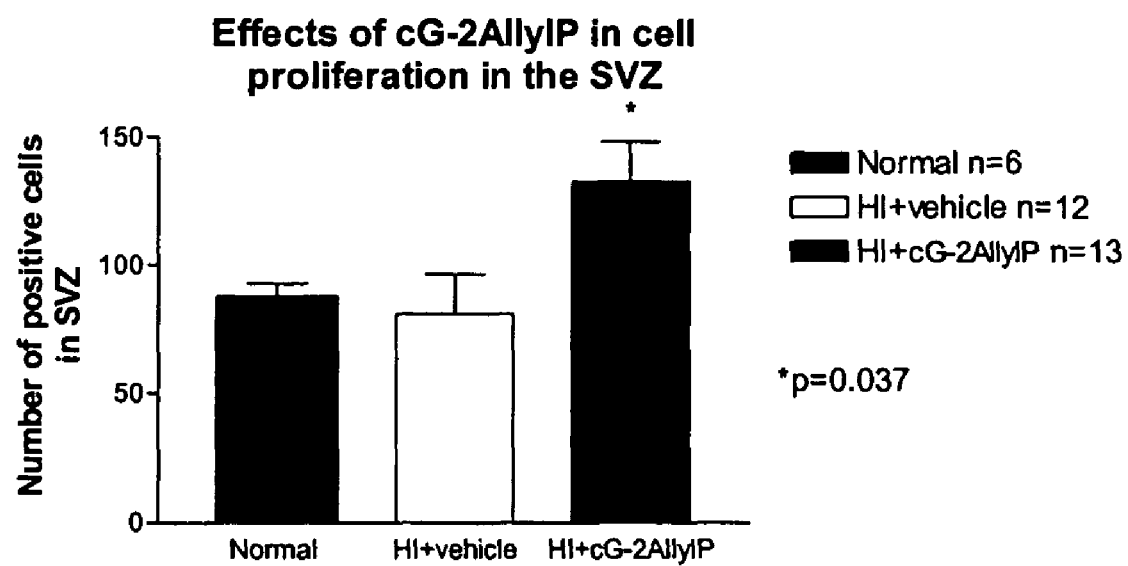
FIG. 5 is a graph showing the effects of cyclic G-2AllylP (66 ng/kg) administered centrally (intra-cerebro-ventricularly, i.c.v.) 2 h after hypoxic-ischemic (HI) injury on the number of proliferating cells in the subventricular zone (SVZ) at 5 days after the HI injury. The treatment with cyclic G-2AllylP significantly increased the number of PCNA-labelled proliferating cells.
Figure 6:
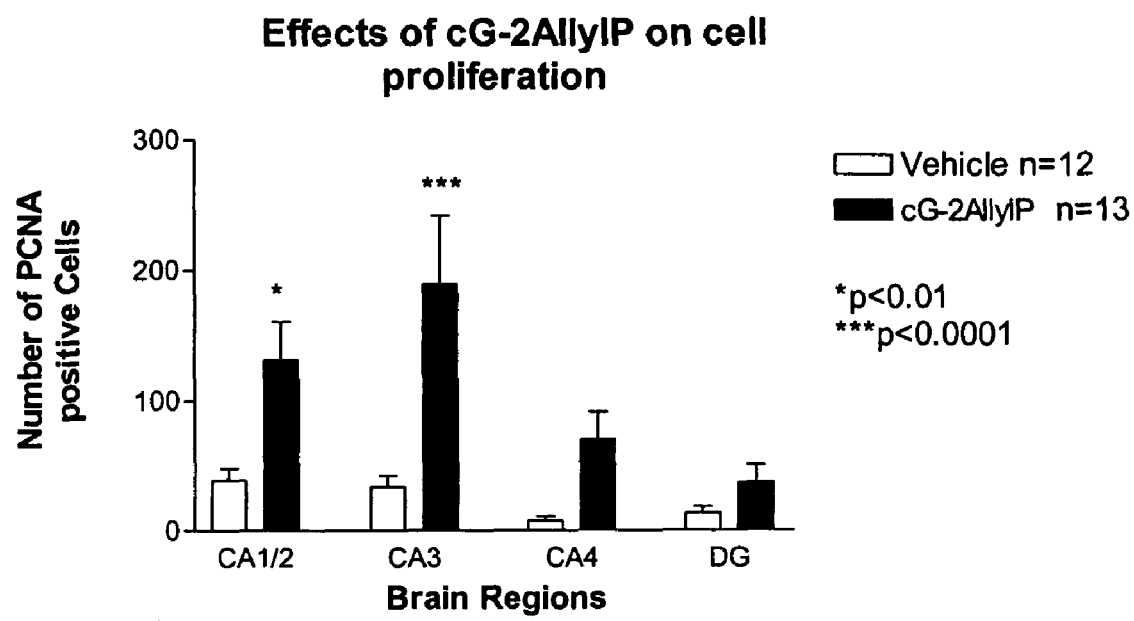
FIG. 6 is a graph showing the effects of cyclic G-2AllylP (66 ng/kg) administered centrally (icv) 2 h after hypoxic-ischemic injury on the number of proliferating cells in the damaged brain regions 5 days after the HI injury. The treatment with cyclic G-2AllylP significantly increased the number of PCNA-labelled proliferating cells, particularly in the CA1/2 and CA3 subregions of the hippocampus.
Figure 7:
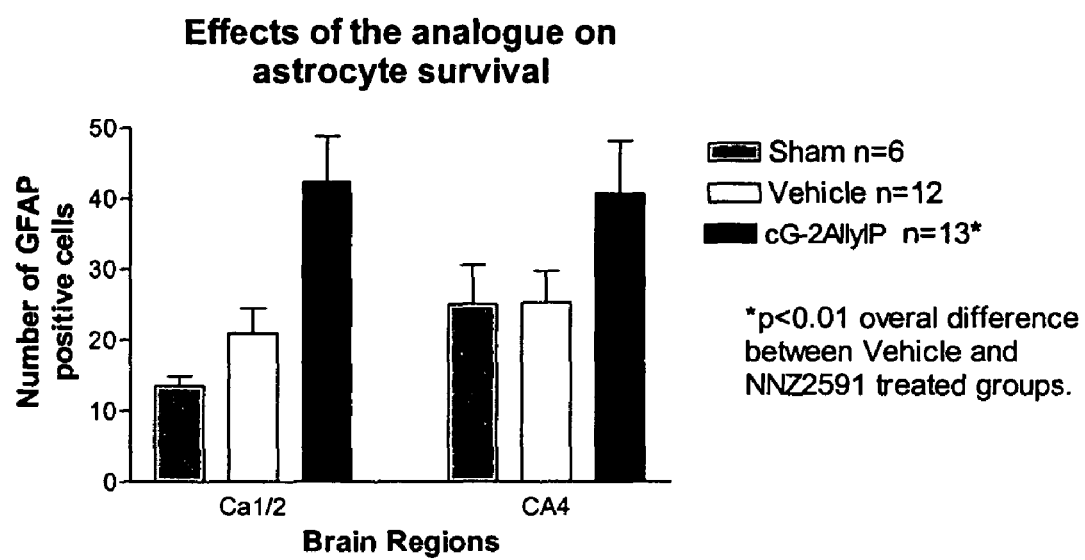
FIG. 7 is a graph showing the effects of cyclic G-2AllylP (66 ng/kg) administered centrally (icv) 2 h after hypoxic-ischemic injury on the number of GFAP-labelled astrocytes in the damaged brain regions 5 days after the HI injury. The treatment with cyclic G-2AllylP slightly increased the number of active GFAP-labelled astrocyte compared to the vehicle-treated group.
Figure 8:
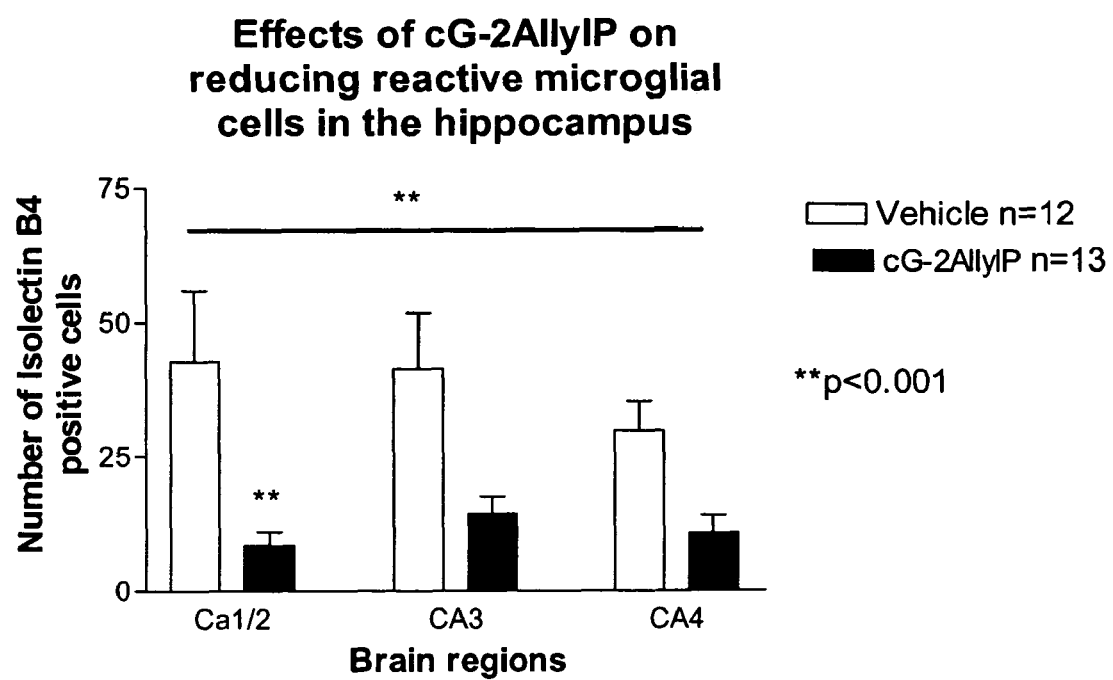
FIG. 8 is a graph showing the effects of cyclic G-2AllylP (66 ng/kg; administered centrally, 2 h after hypoxic-ischemic injury) on the number of isolectin B-4 positive cells (microglia). Treatment with cyclic G-2AllylP reduced significantly the number of active microglia, particularly in the CA1/2 sub-region of the hippocampus.

The cG-2AllylP-treated group showed a significant increase in the number of PCNA-labelled proliferating cells in SVZ (FIG. 5). In the hippocampus, the most significant increase was observed in the CA1/2 and CA3 subregions (FIG. 6). Treatment with cyclic G-2AllylP slightly increased the number of active astrocyte compared to the group treated with vehicle (FIG. 7). Surprisingly, a reduction in the number of active microglia was observed with the largest decrease in the CA1/2 subregion of the hippocampus (FIG. 8).

Conclusion

The results clearly suggest that cG-2AllylP has a proliferative role in adult rats subjected to hypoxic-ischemic injury. In non-treated animals a hypoxic-ischemic injury will normally result in a marked increase in glial cell proliferation. The components of glial cells used for measurement of the increase in proliferation, reactive microlglia and astrocytes, are commonly labelled by isolectin B-4 and GFAP respectively. Surprisingly, in the case of cG-2AllylP treatment there was a reduction in the number of activated microglial cells (FIG. 8) and only a mild increase in the number of astrocytes (FIG. 7). In the light of the significant increase in the number of proliferating cells in the SVZ, it suggests that post-HI treatment with cG-2AllylP leads to proliferation of neuronal progenitors or mature neurons.

Example 9

Central Penetration of cG-2AllylP

Experiment 1: Central Penetration Following HI Injury

Experimental Procedure

Twenty-four male Wistar rats (50-60 days old, weighing between 280-300 g) were used for testing the central penetration of cG-2AllylP following hypoxic-ischemic injury. The animals were subjected to an HI insult described in Example 6 and then treated intraperitoneally (i.p.) with either 3 mg/kg of cG-2AllylP (n=18 with 6 rats in each time points) or its vehicle (normal saline) (n=6) given at 2 hours after hypoxic-ischemic insult. The CSF and plasma were collected for HPLC analysis at 0.5, 2 and 6 hours after the administration of cG-2AllylP.

HPLC Mass Spectroscopy

A HPLC Mass spectrometer system consists of a Surveyor MS pump and Surveyor auto sampler followed by an Ion Max electro spray ionization (ESI) source on a Finnigan TSQ Quantum Ultra AM triple quadrapole mass spectrometer all controlled by Finnigan Xcaliber software (Thermo Electron Corporation).

Methods

A 100 µl sample of plasma was thawed, mixed and filtered through a Nanosep filtration tube with a 3000 MW cut off. (Pall Gellman Laboratory). The filtrate was diluted with water as needed and 5 µl injected on to the HPLC.

The chromatography conditions consisted of a Synergy 4µ MAX-RP 80A column (Phenomenex) 1×50 mm with a mobile phase of 30% Methanol, 0.05% formic acid, balance water flowing at 50 µl per minute with a column temperature of 25° C.

The Mass spectrometry conditions were: ESI in positive mode with a voltage of 5000 V, a sheath gas flow of 50 psi, an auxiliary gas flow of 5 psi, a capillary temperature of 245° C., collision gas of Argon at 0.7 mTorr at a voltage of 40V, with selective reaction monitoring (SRM) transition of 195.15→96 mw. The standard curve was prepared in plasma and was linear from 50-15,000 pg on column.

Results

Figure 9:
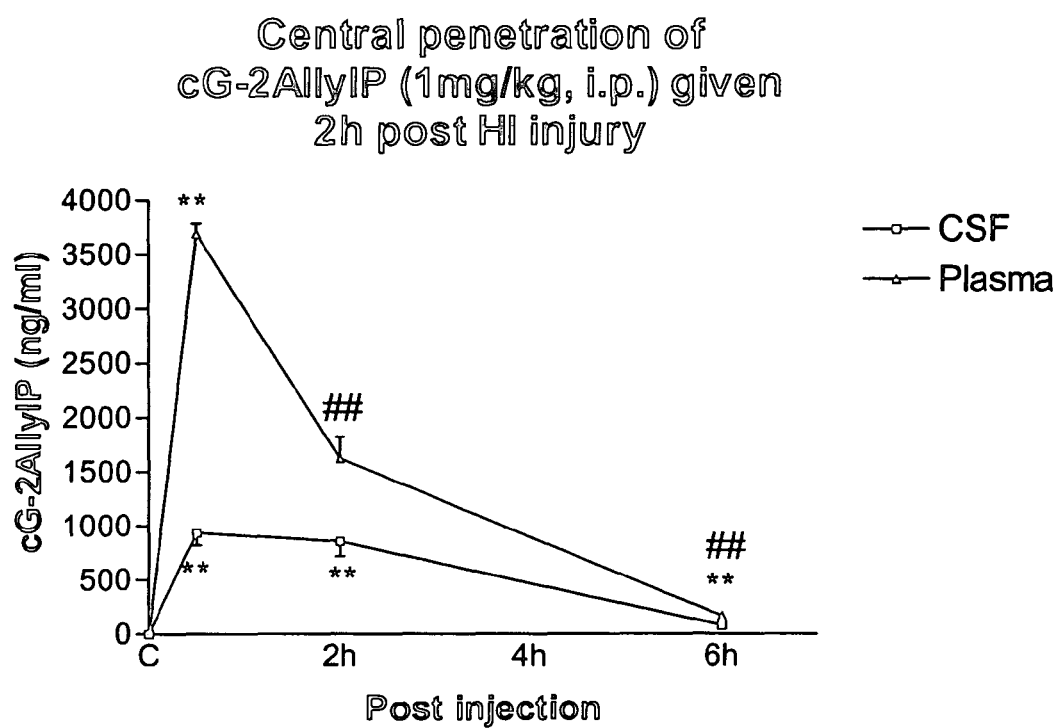
FIG. 9 is a graph showing the penetration of cG-2AllylP (1 mg/kg) into the CSF following i.p. administration of the drug 2 h after HI injury.

Data showed that the level of cG-2AllylP was significantly increased in both plasma and the CSF compared to the controls. The level of cG-2AllylP in the CSF remained in the same level up to 2 h after the i.p. injection (FIG. 9), suggesting cG-2AllylP is highly central assessable.

Experiment 2: Central Penetration Following 6-OHDA Treatment

Experimental Procedures

Nine rats were used for testing central uptake of cG-2AllylP in the 6-OHDA rat model of Parkinson's disease. cG-2AllylP (3 mg/kg) was administered i.p. at 2 h following the 6-OHDA lesion (n=6) and to normal control rats (n=3). The CSF and the plasma were collected 2 hours after the i.p. administration. The samples were analysed using HPLC as described above.

Results

Figure 10:
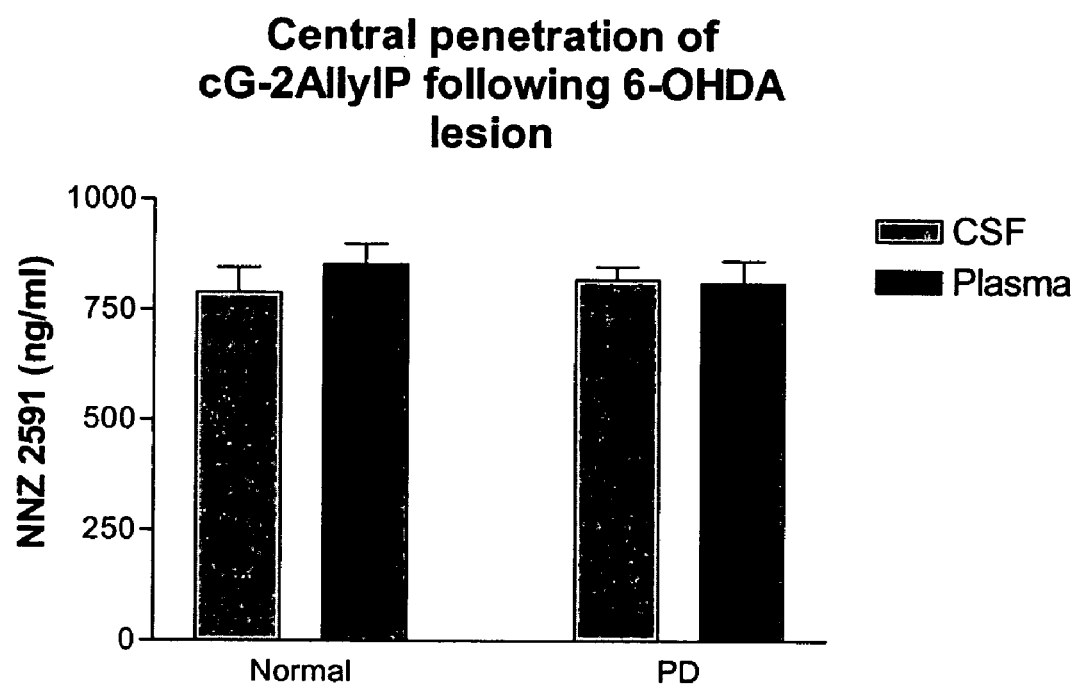
FIG. 10 is a graph showing the penetration of cG-2AllylP (1 mg/kg) into the CSF following an i.p. administration of the drug 2 h after 6-OHDA treatment.

The data showed that the level of cG-2AllylP in the CSF were similar to that found in the plasma (FIG. 10), suggesting 100% central penetration at 2 hours post i.p. administration. A similar central penetration was found between the normal and PD rats suggesting the BBB did not alter the central penetration of cG-AllylP.

Example 10

Effects of cG-2AllylP in 6-OHDA Model of Parkinson's Disease

Experimental Procedures

6-OHDA Model 6-hydroxydopamine (6-OHDA) was prepared as 7 ug in a base of 2 ul 0.9% saline containing 1% ascorbic acid and administered in two injections into the striatum using coordinates [for injection 1: AP+8 mm, lateral R 3 mm and ventral−6 mm and (b) for injection 2: AP+7 mm, lateral R 3.5 mm and vertical−6.5 mm] under anaesthesia of 3% halothane. The 6-OHDA was injected using Hamilton syringe (100 ul with 30 G needle) controlled by a microdialysis infusion pump at an infusion rate of 0.2 ul/min.

In rats, 6-OHDA injection into the lateral striatum of anaesthetised animals stereotaxicaly, leads to a rapid onset and progressive loss of the nigra dopaminergic neurones and depletion of nigro-striatal neurotransmission. This elegantly models the loss of the same neuronal pathway that degenerates over time in Parkinson's disease. Lesioned rats display a degenerate dopaminergic function, and because they receive 6-OHDA to only one side of the brain in the model, they show unilateral motoric impairments. The laterality of the model therefore enables ipsilateral to contralateral comparison of function within-subject. Two common approaches are taken to assess the pharmacological restoration of function in the model; one is to measure the degree of rotational activity for nigro-striatal dopamine transmission and the second is to assess the parkinsonian motor deficit in impaired (contralateral) limb, such as the adjusted step test. cG-2AllylP was tested for its capacity to recover from 6-OHDA induced parkinsonian motor deficit using the adjusting step test.

Adjusted Step Test

This test assesses the use of the impaired side limb to place a paw down as the rat is encouraged to move laterally along a 1 m long run. Ipsilateral steps (the uninjured side) are made as often as is necessary to maintain balance and speed, which normally rats make average 15 steps during each test. The impaired side step is often make less steps due the slowness in adjusting the body position. By assessing the ratio of contralateral to ipsilateral steps made, a measure of Parkinsonian motoric deficit can be increased. All animals were habituated with the test before the lesion was induced. The data is presented as left/right ratio in the steps and 100% represents normal function.

Experiment 1: Effect of cG-2AllylP Treatment on Development of Parkinsonian Motor Deficits in 6-OHDA-Treated Animals Experimental Procedures cG-2AllylP was tested in the 6-hydroxydopamine (6-OHDA) model of Parkinson's disease. Sixteen male Wistar rats (50-60 days, 280-300 g) were used for the study. 2 hours following the induction of the lesion each animal received either single dose of cG-2AllylP (20 ng/rat; 66 ng/kg; n=8) or the same volume of vehicle (normal saline). The drug and the vehicle were given centrally (delivered to the CSF by icv administration). The adjusted step tests were performed on both groups at weeks 0 (pre-lesion), 2, 4, 6, 8, 10 and 12 from the lesion.

Results

Figure 11:
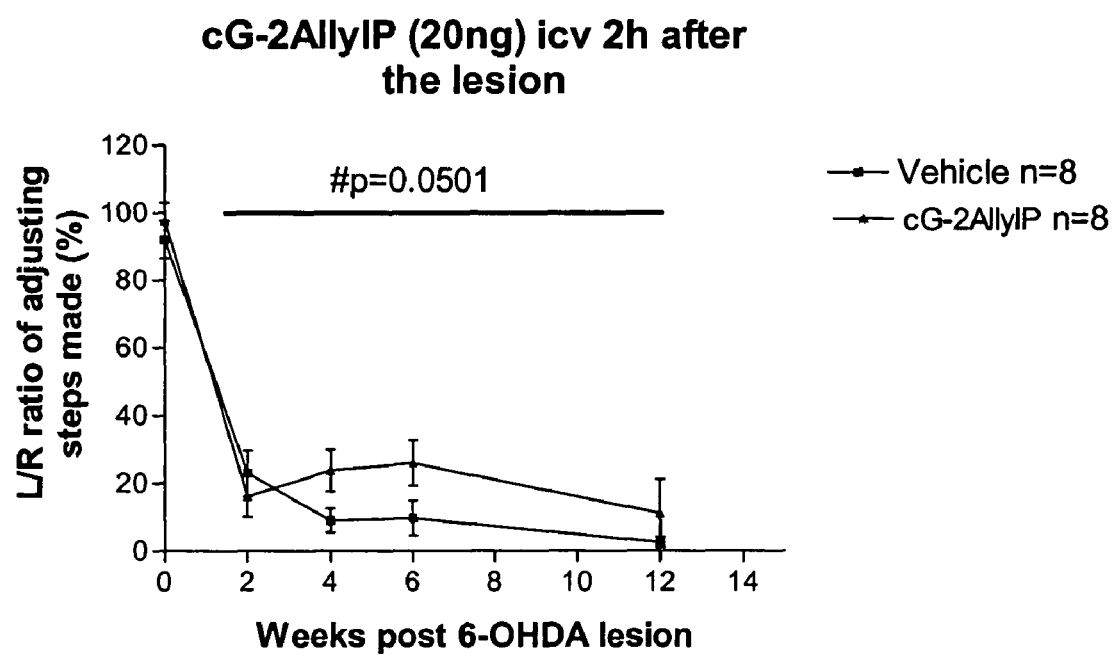
FIG. 11 is a graph showing the effects of a single dose of cyclic G-2AllylP (20 ng/rat i.e. 66 ng/kg, delivered into the CSF circulation 2 h after the 6-OHDA treatment) on motor competence in the adjusted step test. Significant improvement was observed in the cG-2AllylP treated group (n=8) in the 4 to 6 weeks following the 6-OHDA treatment while the motor deficits in the vehicle treated group (n=8) increased during that period.
Figure 12:
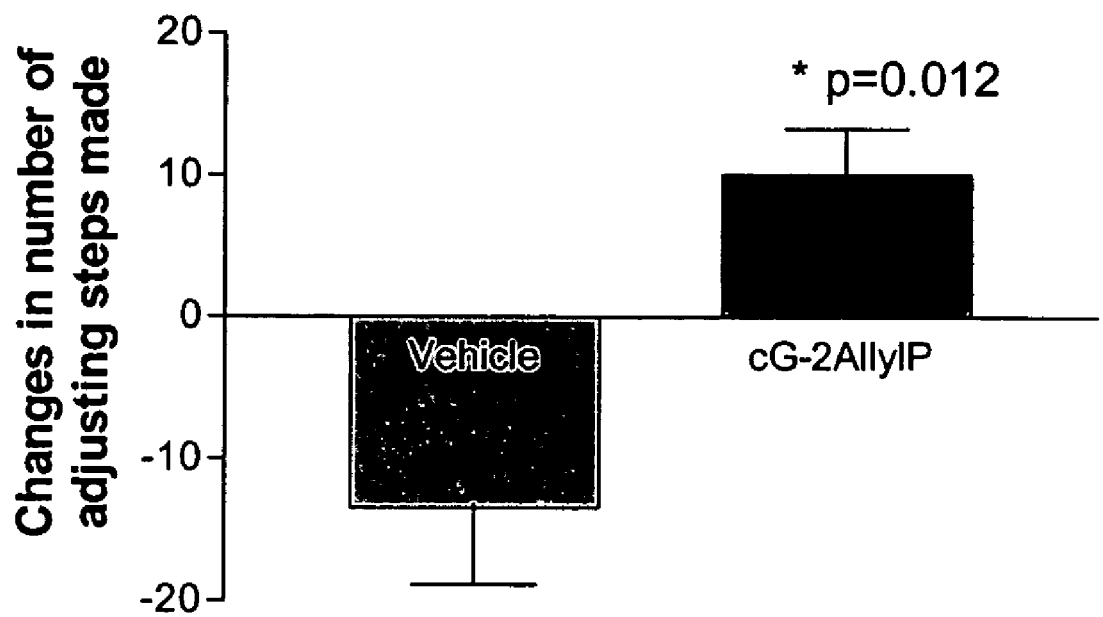
FIG. 12 is a graph showing the comparison between the motor deficits, measured in recovery of adjusted steps, in the vehicle-treated group (n=8) and the cG-2AllylP-treated group (n=8) during the period from $2^{nd}$ to $6^{th}$ week after 6-OHDA treatment.

The cG-2AllylP-treated group displayed functional recovery from week 2 to week 6 (FIG. 11; p=0.05). The changes in the number of adjusted steps made by the treated and the non-treated animals in the period between week 2 and week 6 were presented in FIG. 12 (p=0.012).

Conclusion

In contrast with other preventive treatments, which are expected to only reduce the functional deficit, treatment with cG-2AllyP promotes recovery. The improved function was seen for an extended period of time following the single dose treatment. This may suggest that the compound may encourage repair mechanisms rather than preventive mechanisms.

Experiment 2: Effect of Multiple Doses of cG-2AllylP on Functional Recovery from Motor Deficits in 6-OHDA-Treated Animals Experimental Procedures In order to test whether cG-2AllyP promotes the functional recovery from motor deficits, we analysed the effects of a delayed multiple dose treatment with cG-2AllylP on rats treated with 6-OHDA.

Six adult male Wistar rats (50-60 days old, 280-300 g) were used for the study. All rats were habituated with the adjusted step test as described above. Then the 6-OHDA was induced. The motor deficits of each animal were tested at 2 weeks after the induction of the lesion, when the motor deficit fully developed in all animals. Rats were divided into the vehicle and cG-2AllylP treated group. The treatment was administered in week 2-3. The treatment 20 ng/animal/day of cG-2AllylP was given icv 5 days. The motor deficits were tested using adjusted step tests at week 4, 6 and 8. The cG-2AllylP group showed an improvement in the adjusted step test from week 4 and the effect lasted until the end of experiment.

Results

Figure 13:
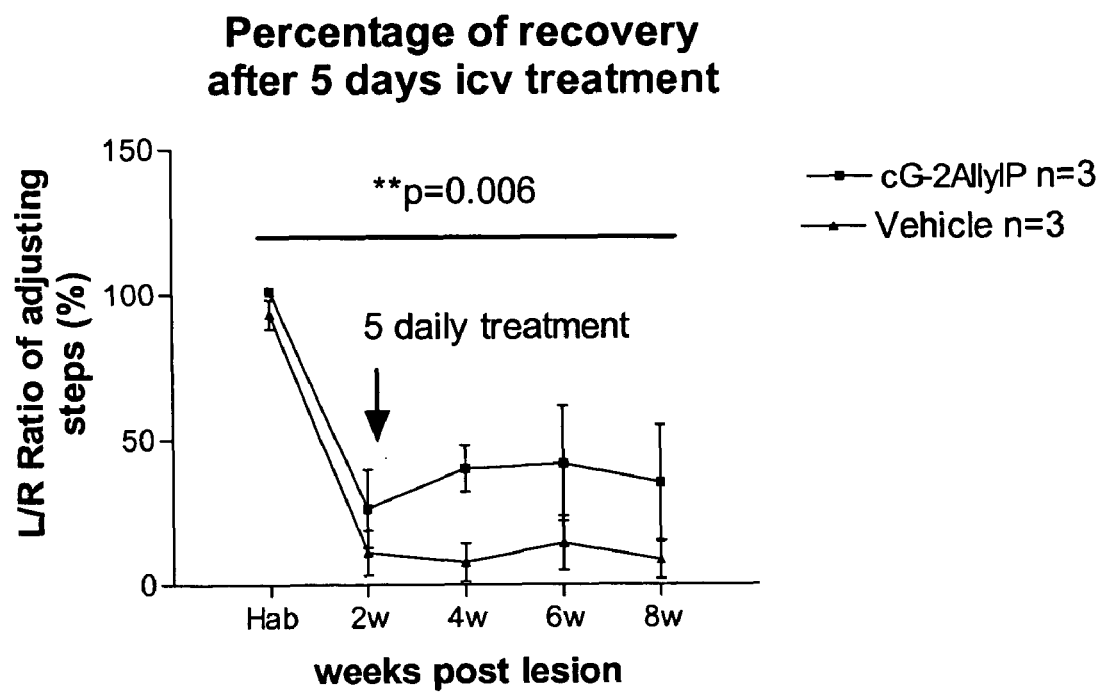
FIG. 13 is a graph showing the effects of cG-2AllylP treatment (66 ng/kg/day, icv, for 5 days) commencing at 2 weeks after the 6-OHDA treatment on motor competence in the adjusted step test. The treatment group (n=3) showed significant improvement over the vehicle group (n=3) in motor function at 4 weeks after 6-OHDA treatment (2 weeks after treatment with cyclic G-2AllylP) and the effect lasted until the termination of the experiment at week 8. (p=0.006).

The cG-2AllylP-treated group displayed similar patter to the drug-treated group in Experiment 1 (FIG. 13, p=0.006).

Experiment 3: Effect of cG-2AllylP on Functional Recovery in 6-OHDA-Treated Rats Following Peripheral Administration Experimental Procedures Thirty-six adult male Wistar rats (50-60 days old, 280-300 g) were used for testing the effects of cG-2AllylP on long-term functional recovery following delayed treatment. All rats were habituated with the adjusted step test as described above. On day 1 rats underwent the 6-OHDA lesion induction surgery as described above. The motor deficits were tested in the adjusted step tests at 2 weeks after the lesion. Rats were then divided into four treatment groups (vehicle, and cG-2AllylP treatment groups: 0.2 mg/rat, 1 mg/rat and 5 mg/rat, i.p.) depending on the behavioural deficit detected. The one week daily treatments with cG-2AllylP were carried out between 2-3 weeks after the lesion. The adjusted step tests were carried out at 6, 7, 9 and 11 weeks after the lesion (3, 4 and 6 and 8 weeks after the completion of the cG-2AllyP treatment).

Results

Figure 14:
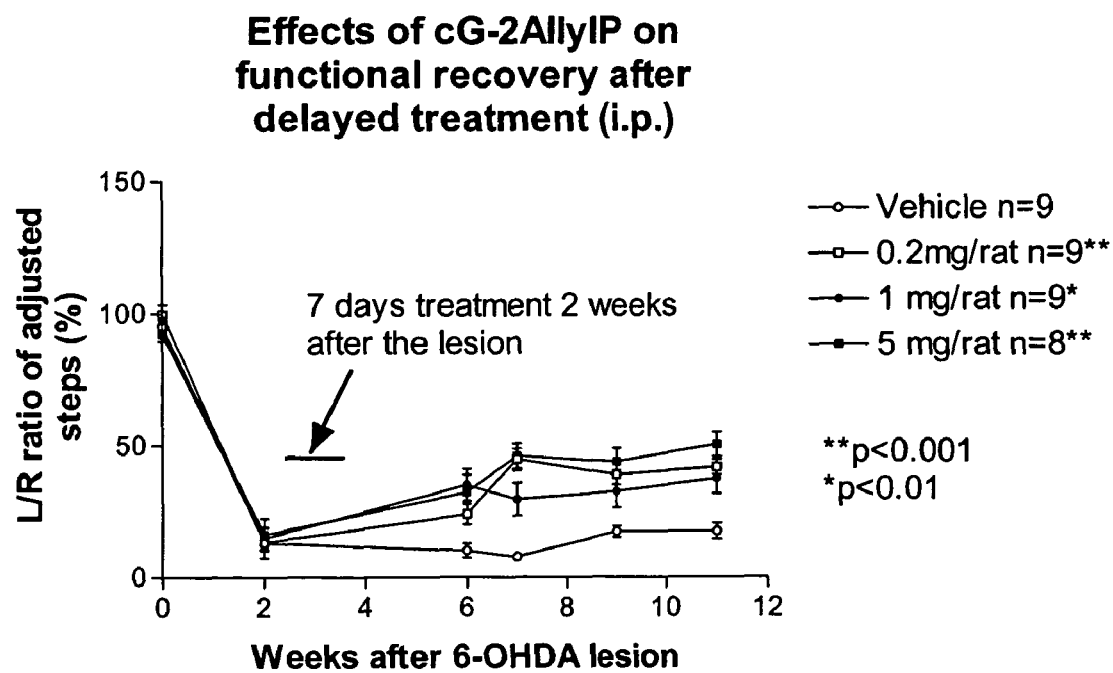
FIG. 14 is a graph showing the effect of cG-2AllylP on motor competence in the adjusted steps test using 6-OHDA-treated rats. Seven days' treatment with cG-2AllylP during week 3 of the experiment resulted in an improved performance during testing at the end of weeks 6, 7, 9, and 11.

Cyclic G-2AllylP significantly improved performance in the step-test even though drug was not given until 14 days following the lesion (FIG. 14).

With all three doses there was an improvement in the motor function compared to the vehicle treated group. The improvement in the group treated with the highest dose (5 mg/kg) was the most significant. These data suggest that cG-2AllylP may improve Parkinsonian symptomology once the damage has occurred, perhaps by inducing restoration of neuronal function within the nigro-striatal system. The effect of cG-2AllylP is unusual for an anti-Parkinsonian agent, which are usually observed to either (a) acutely prevent lesion development, or (b) only show beneficial motoric effects when drug is "on-board". In the study shown here, drug was given for 7 days, but testing occurred on repeat occasions many weeks later. This suggests that the effects of the drug on executive motor function are long lasting, and may result from DKP-induced effects on neuronal growth and connectivity as opposed to a simple pharmacological consequence.

Example 11

Pharmacokinetics of Cyclic G-2 Allyl Proline

Figure 15A:
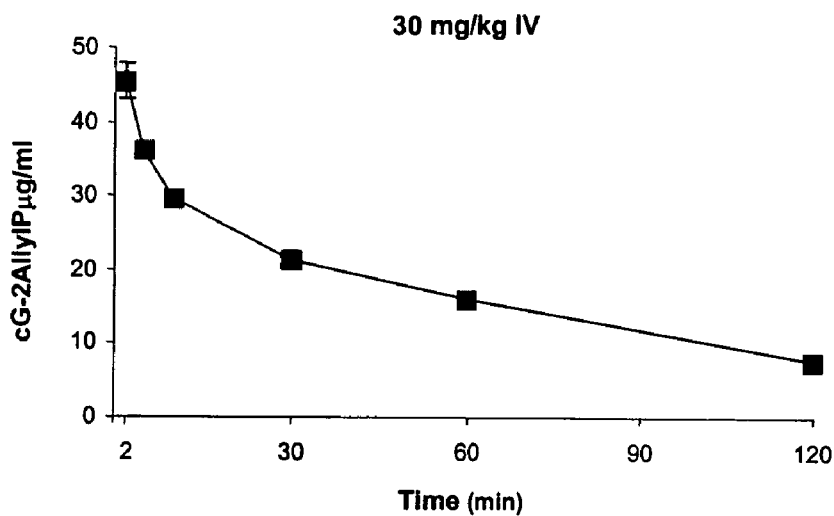
FIGS. 15A and 15B show graphs of plasma concentrations of cG-2AllylP after intravenous administration (FIG. 15A) or after oral administration (FIG. 15B).
Figure 15B:
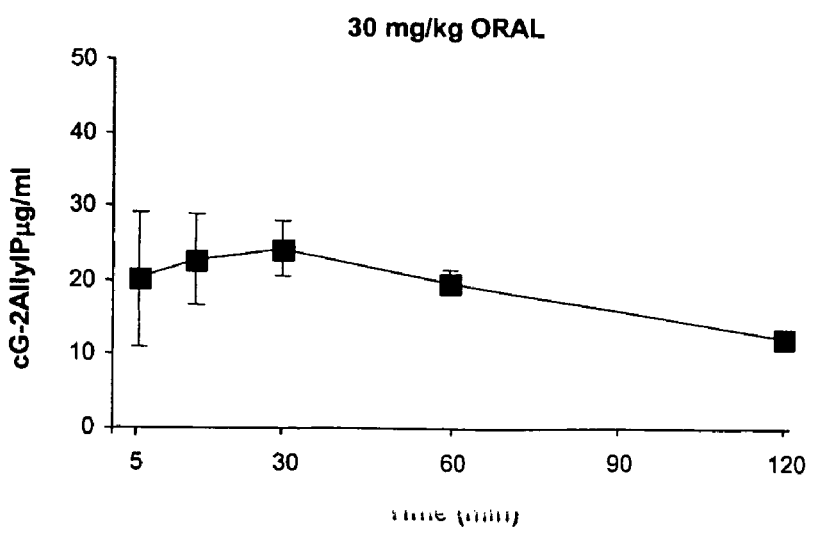

To determine whether cG-2AllylP has pharmacokinetics suitable for therapeutic application, we compared plasma concentrations of cG-2AllylP after intravenous or oral administration. FIG. 15A shows a graph of plasma concentration of cG-2AllylP versus time after intravenous injection of 30 mg/kg of cG-2AllylP. The graph shows approximately first-order kinetics, with an elimination half-life of about 50.0 minutes. FIG. 15B shows a graph of cG-2AllylP concentration versus time after oral administration of 30 mg/kg. In contrast with the results shown in FIG. 15A, by 5 minutes after oral administration, the plasma concentration of cG-2AllylP had reached a significant level (approximately 20 μg/ml) and thereafter increased slowly to a maximum of about 25 μg/ml. Subsequently, for the next 90 minutes, the plasma concentration of cG-2AllylP decreased in an approximately linear fashion and that 2 hours after oral administration, the plasma concentration was greater than 10 μg/ml.

We conclude from this study, that plasma concentrations of cG-2AllylP can be reached after intravenous or after oral administration, and that sustained, relatively consistent concentrations of cG-2AllylP can be achieved after oral administration.

This invention is described with reference to specific embodiments thereof. Other features and embodiments of this invention can be produced by those of skill in the art without undue experimentation and a reasonably likelihood of success. All of those embodiments are considered to be part of this invention.

We claim:

1. A composition comprising cyclic Glycyl-2-Allyl Proline having the formula:

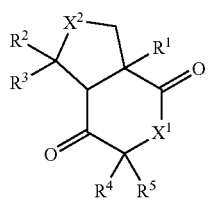

or a pharmaceutically acceptable salt, or stereoisomer thereof, wherein $R^1$=allyl, $R^2$=$R^3$=$R^4$=$R^5$=H, $X^1$=NH, $X^2$=$CH_2$ in a physiologically compatible form.

2. The composition of claim 1, comprising an aqueous solution and one or more pharmaceutically acceptable excipients, additives, carriers or adjuvants.

3. The composition of claim 1, further comprising one or more excipients, carriers, additives, adjuvants or binders in a tablet or capsule.

4. A method for treating an animal having Parkinson's disease and an abnormality of neurological function, comprising administering to said animal, a composition comprising an effective amount of cyclic Glycyl-2-Allyl Proline.

5. The method of claim 4, wherein said abnormality of neurological function is a motor abnormality or cognitive abnormality.

6. The method of claim 4, wherein said cyclic G-2AllylP is administered via an oral, intraperitoneal, intravascular, peripheral circulation, intracerebral-ventricular, subcutaneous, intraorbital, ophthalmic, intraspinal, intracisternal, topical, infusion, implant, aerosol, inhalation, scarification, intraperitoneal, intracapsular, intramuscular, intranasal, buccal, transdermal, pulmonary, rectal or vaginal route.

7. The method of claim 4, wherein said effective amount of cyclic G-2AllylP has:
    a lower limit of about 0.001 milligrams per kilogram mass (mg/kg) of the animal; and
    an upper limit of about 100 mg/kg.

8. The method of claim 4, further comprising administration of one or more neuroprotective agents selected from the group consisting of insulin-like growth factor-I (IGF-I), insulin-like growth factor-II (IGF-II), transforming growth factor-β1, glycyl-prolyl-glutamate, glycyl-2-methyl prolyl glutamate, activin, growth hormone, nerve growth factor, growth hormone binding protein, IGF-binding proteins, IGFBP-3, basic fibroblast growth factor, acidic fibroblast growth factor, the hst/Kfgk gene product, FGF-3, FGF-4, FGF-6, keratinocyte growth factor, androgen-induced growth factor, int-2, fibroblast growth factor homologous factor-1 (FHF-1), FHF-2, FHF-3 and FHF-4, keratinocyte growth factor 2, glial-activating factor, FGF-10 and FGF-16, ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukaemia inhibiting factor, oncostatin M, interleukin), α-interferon, β-interferon, γ-interferon, consensus interferon, and TNF-α, kynurenic acid, Semax, tacrolimus, L-threo-1-phenyl-2-decanoylamino-3-morpholino-1-propanol, andrenocorticotropin-(4-9) analogue (ORG 2766), dizolcipine (MK-801), selegiline; glutamate antagonists, NPS1506, GV1505260, MK-801, GV150526; AMPA antagonists, 2,3-dihydroxy-6-nitro-7-sulfamoylbenzo(f)quinoxaline (NBQX), LY303070, LY300164; anti-inflammatory agents, addressin MAdCAM-1, integrin α4 receptors (α4β1 and α4β7) and anti-MAd-CAM-1 mAb MECA-367 (ATCC accession no. HB-9478).

9. The method of claim 4, wherein said cyclic G-2AllylP is administered at a time during which an adverse neurological symptom of Parkinson's disease is present.

10. The method of claim 4, wherein said cyclic G-2AllylP is administered at a time during which an adverse symptom of Parkinson's disease is not present.

11. The method of claim 9, wherein said adverse neurological symptom of Parkinson's disease is a motor deficit or a cognitive deficit.

12. The method of claim 10, wherein said adverse neurological symptom of Parkinson's disease is a motor deficit or a cognitive deficit.

13. The method of claim 4, further comprising administering another neuroprotective agent.

* * * * *

UNITED STATES PATENT AND TRADEMARK OFFICE
CERTIFICATE OF CORRECTION

PATENT NO. : 7,776,876 B2
APPLICATION NO. : 11/399974
DATED : August 17, 2010
INVENTOR(S) : Margaret Anne Brimble et al.

Page 1 of 1

It is certified that error appears in the above-identified patent and that said Letters Patent is hereby corrected as shown below:

In the Claims

Column 34, line 40, Claim 8: after "interleukin", delete ")".

Signed and Sealed this
Sixteenth Day of July, 2013

Teresa Stanek Rea
*Acting Director of the United States Patent and Trademark Office*